United States Patent [19]

Cross et al.

[11] 4,058,391

[45] Nov. 15, 1977

[54] 1,2-DIALKYL-3,4,5-TRISUBSTITUTED PYRAZOLIUM SALTS AS HERBICIDAL AGENTS

[75] Inventors: Barrington Cross, Rocky Hill; Bryant Leonidas Walworth, Pennington, both of N.J.

[73] Assignee: American Cyanamid Company, Stamford, Conn.

[21] Appl. No.: 657,114

[22] Filed: Feb. 11, 1976

Related U.S. Application Data

[60] Division of Ser. No. 584,686, June 6, 1975, Pat. No. 3,963,742, which is a continuation-in-part of Ser. No. 487,826, July 12, 1974, abandoned.

[51] Int. Cl.² .............................................. A01N 9/22
[52] U.S. Cl. .......................................... 71/92; 71/86
[58] Field of Search ........................... 71/92; 260/311; 424/273

[56] References Cited

U.S. PATENT DOCUMENTS

| | | | |
|---|---|---|---|
| 3,326,662 | 6/1967 | Toyosato et al. | 71/92 |
| 3,922,161 | 11/1975 | Walworth et al. | 71/92 |
| 3,925,408 | 12/1975 | Cross | 71/92 |

OTHER PUBLICATIONS

Nye et al., "Tautomerism of 4-hydroxypyrazoles, etc." (1971), Tetrahedron 28, pp. 455–462 (1972).
Elguero et al., "No. 302 Recherches dans la serie, etc." (1968), Bull. Soc. Chim. Fr., pp. 1687–1698 (1969).
Laboratoire Cetrane, "Antidiabetic 3-pyrazolines." (1973), CA 80, No. 120,928g. (1974).

*Primary Examiner*—Glennon H. Hollrah
*Attorney, Agent, or Firm*—Harry H. Kline

[57] ABSTRACT

There are provided 1,2-dialkyl-3,4,5-trisubstituted pyrazolium salts which are useful as herbicidal agents as well as a method for the preparation of the said pyrazolium salts.

9 Claims, No Drawings

1,2-DIALKYL-3,4,5-TRISUBSTITUTED PYRAZOLIUM SALTS AS HERBICIDAL AGENTS

This application is a divisional of our copending application, Ser. No. 584,686, filed on June 6, 1975, now U.S. Letters Pat. No. 3,963,742, issued on June 15, 1976 which application is a continuation-in-part application of our application, Ser. No. 487,826, filed on July 12, 1974, now abandoned.

BACKGROUND 1,2-Dialkyl-3,5-diphenylpyrazolium salts and their use as herbicidal agents, particularly as herbicidal agents effective for the selective control of wild oats (*Avena spp.*) in the presence of certain small grains, is disclosed in the Klingsberg et al. Netherlands application No. 72-17,015, published on June 19, 1973.

Although the 1,2-dialkyl-3,5-diphenylpyrazolium salts in the above-mentioned reference are uniquely effective for selective control of wild oats, said compounds generally exhibit only minimal herbicidal activity against other economically important grass weeds such as barnyardgrass, foxtail and crabgrass.

It would, therefore, be desirable if a compound could be found which would provide selective control of the aforementioned undesirable grasses.

Surprisingly, it has been found that the substitution in the 4- position of the pyrazolium ring in place of hydrogen, particularly by alkoxy, markedly alters the spectrum of postemergence herbicidal activity of the desired pyrazolium compounds. Such alteration changes the biological activity of the latter compounds by providing them with a much broader spectrum of broadleaf weed and of grass control and the most noteworthy changes are seen in the pronounced improvement in Sesbania, mustard, pigweed, morningglory and barnyardgrass control and the selectivity obtained when said compounds are used for grass control in the presence of rice.

SUMMARY OF INVENTION

The invention relates to novel 1,2-dialkyl-3,4,5-trisubstituted pyrazolium salts represented by the structure

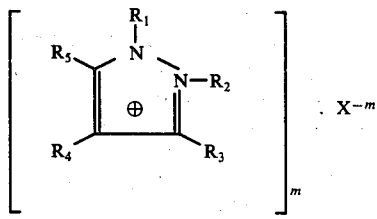

wherein $R_1$ represents a member selected from the group consisting of alkyl $C_1$–$C_5$ straight chain or branched, allyl and benzyl; $R_2$ is alkyl $C_1$–$C_5$ straight chain or branched; $R_3$ represents a member selected from the group consisting of

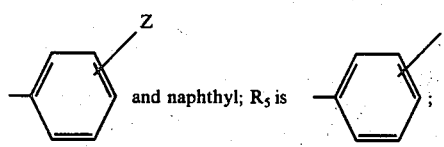

and naphthyl; $R_5$ is $R_4$ represents a member selected from the group consisting of alkoxy $C_1$–$C_{22}$ straight chain or branched, alkenyloxy $C_3$–$C_4$ straight chain or branched and optionally substituted with halogen, alkynyloxy $C_3$–$C_4$ straight chain or branched, —O—$(CH_2)_n$—W, alkylthio $C_1$–$C_{22}$ straight chain or branched, alkylsulfonyl $C_1$–$C_{22}$ straight chain or branched,

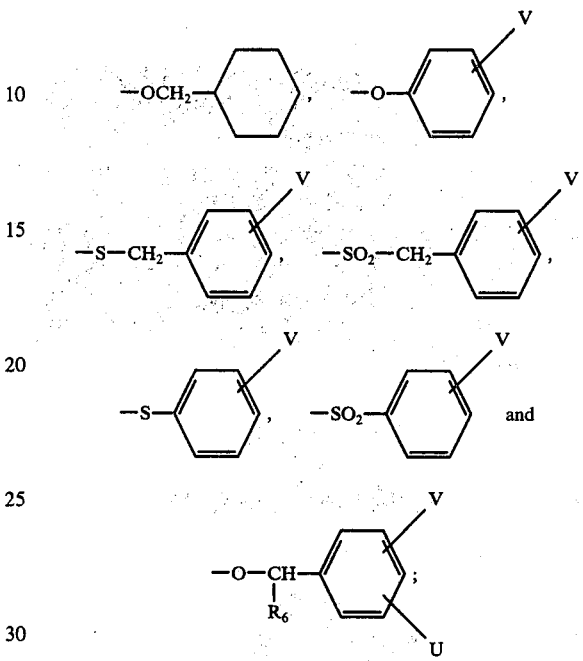

$R_6$ represents a member selected from the group consisting of hydrogen, methyl and phenyl; U and V each represent members independently selected from the group consisting of hydrogen, halogen, alkyl $C_1$–$C_4$, alkoxy $C_1$–$C_4$, $NO_2$ and $CF_3$; W represents a member selected from the group consisting of halogen, cyano, carbalkoxy $C_1$–$C_7$ straight chain or branched,

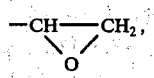

alkoxy $C_1$–$C_7$ straight chain or branched, alkylthio $C_1$–$C_7$ straight chain or branched, alkylsulfonyl $C_1$–$C_7$ straight chain or branched, benzylthio and benzylsulfonyl; Z and Z' each represent members selected from the group consisting of hydrogen, halogen, alkyl $C_1$–$C_{12}$ straight chain or branched, alkoxy $C_1$–$C_4$ straight chain or branched and phenyl; X represents an anion with a charge of from 1 to 3, and preferably 1 or 2; m represents an integer selected from the group consisting of 1, 2 and 3, and preferably 1 or 2; n represents an integer selected from the group consisting of 1, 2, 3 and 4.

The term "halogen" as used herein is intended to mean fluorine, chlorine, bromine and iodine.

Illustrative of the anions which are suitable for use in the present invention are halides such as chloride, bromide and iodide; triodide; tribromide; tetrafluoroborate; hydroxide; acetate; sulfate; hydrogen sulfate; methyl sulfate; benzene sulfonate; perchlorate; $C_1$–$C_4$ alkyl benzene sulfonate, preferably p-toluenesulfonate; hydrogen phosphate; $C_1$–$C_4$ alkane sulfonate;

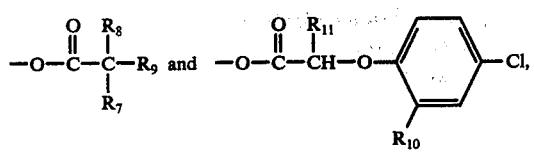

where $R_7$ and $R_8$ are halogen; $R_9$ is halogen, methyl, halomethyl or dihalomethyl; $R_{10}$ is chlorine or methyl; and $R_{11}$ is hydrogen or methyl.

Preferred compounds of this invention have the above structure, wherein $R_1$ and $R_2$ are each methyl or ethyl; $R_3$ and $R_5$ are each phenyl; $R_4$ is a member selected from the group consisting of $OCH_3$, $OC_2H_5$, $OC_3H_7$-n, $OCH_2C\equiv CH$, $OC_4H_9$-n, $OC_5H_{11}$-n, $OC_6H_{13}$-n, $OC_{13}H_{27}$-n, $OC_{16}H_{33}$-n, $O(CH_2)_2Br$, $OCH_2CH=CHCl$,

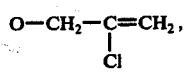

$OCH_2OC_7H_{15}$-n, $SC_4H_9$-n, and the moiety:

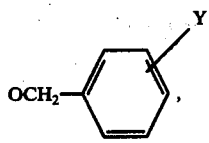

where Y is selected from the group consisting of hydrogen, 4-methyl, 3-chloro, 4-chloro and 3-$CF_3$; $m$ is 1; and X represents an anion selected from the group consisting of methyl sulfate, bromide, chloride, iodide, perchlorate, phosphate, hydrogen phosphate, hydrogen sulfate and p-toluenesulfonate.

Further, especially preferred compounds have the above structure, where $R_1$ and $R_2$ each represent methyl; $R_3$ and $R_5$ are each phenyl; $R_4$ is methoxy, ethoxy, n-propoxy, benzyloxy or hexadecyloxy; $m$ is 1; and X is methyl sulfate, chloride, hydrogen phosphate, bromide, iodide, hydrogen sulfate or p-toluenesulfonate.

In accordance with this invention compounds having the structure (I):

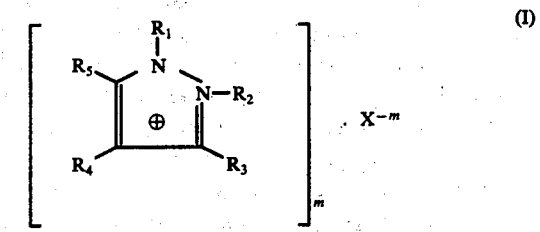

wherein $R_1$, $R_2$, $R_3$, $R_4$, $R_5$, X and $m$ are as described above, can be prepared by N-alkylation of a formula (II) pyrazole or O-alkylation of an alkali metal salt of a pyrazolium hydroxide (III). These reactions may be graphically illustrated as follows:

Method A

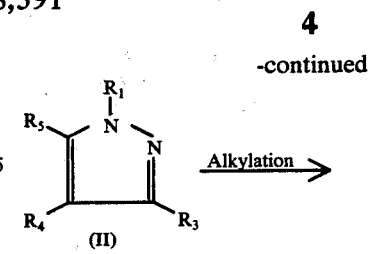

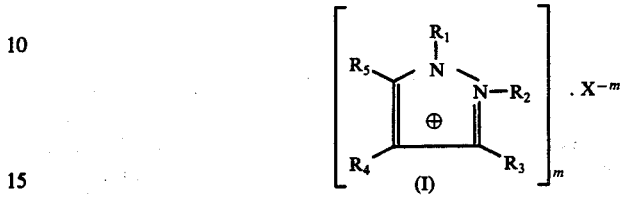

Method B

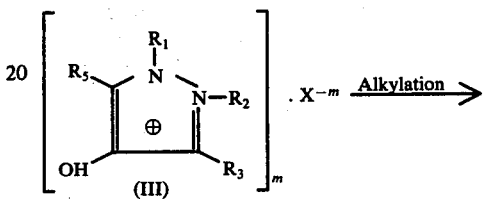

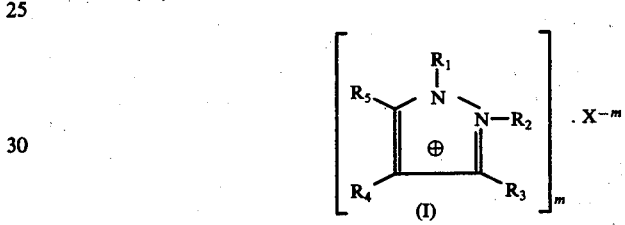

wherein $R_1$, $R_2$, $R_3$, $R_4$, $R_5$, $m$ and X are as described above.

In accordance with the procedure of Method A, a pyrazole such as depicted by formula II can be alkylated in toluene, xylene or similar solvent, with one or more equivalents of an alkylating agent such as dimethyl sulfate, methyl iodide, methyl bromide or p-methyl toluene sulfonate. This reaction is generally carried out at a temperature between 70° C and 150° C, and preferably, at a temperature between 70° C and 130° C.

Suitable alkylating agents include alkyl halides, alkyl sulfates, dialkyl sulfates, alkyl phosphates, alkyl hydrogen sulfates, and alkyl toluene sulfonates; with these alkylating agents, said alkyl groups each have 1 to 4 carbon atoms. Among the preferred alkylating reagents are the alkyl halides such as methyl, ethyl, n-propyl, isopropyl, n-butyl, isobutyl and allyl chloride or iodides; alkyl sulfates, dialkyl sulfates, alkyl hydrogen sulfates and toluene sulfonates.

In carrying out the alkylation reaction, it may be expedient to initially form a salt having an anion other than that which it is desired to employ in the herbicidal processes of the present invention. In such cases, the exchange in anion may be conveniently made in a subsequent step.

The exchange can be effected by treating the initially formed salt with an ion exchange resin. Among the suitable ion exchange resins, one may mention a strong base organic anion exchanger such as Dowex 1-X8 which is a quaternary alkyl ammonium resin. Where the resin is supplied as the salt of an anion other than that desired, it is pretreated with an aqueous solution of a salt of the desired anion. For example, if the resin is supplied as a quaternary ammonium chloride and it is desired to produce a pyrazolium nitrate, one would pretreat the resin with an aqueous solution of sodium nitrate.

Exchange of the anion X, in the formula (I) pyrazolium salt, can also be achieved directly by exchange with an appropriate acid, e.g. the methyl sulfate can be exchanged for the bromide, iodide or perchlorate anion, by treatment thereof with aqueous hydrobromic acid, aqueous hydriodic acid or aqueous perchloric acid, respectively. In addition, the methyl sulfate can be exchanged for other anions such as $CL^-$, $NO_3^-$ or $CH_3COO^-$, by adding to an aqueous solution of the methyl sulfate salt such salts as calcium chloride, calcium nitrate or calcium acetate, either as a salt or as an aqueous solution. Insoluble calcium methyl sulfate precipitates and is removed by filtration. The desired pyrazolium salt can be isolated as a solid from the aqueous medium by extraction with chloroform and then removal of the chloroform by evaporation.

The bromides or iodides may also be conveniently converted to the tribromides or triodides by addition of bromine or iodine to a solution of the monobromide or monoiodide in a solvent such as ethanol.

An alternative method for the preparation of the formula (I) pyrazolium salts, wherein $R_4$ is as hereinbefore defined is described above and identified as Method B. This preparative method involves the alkylation of an alkali metal salt of a formula (III) pyrazolium salt and is generally carried out in the presence of an aprotic solvent such as dimethylformamide (DMF), dimethylsulfoxide (DMSO), xylene, toluene, benzene, or the like, at a temperature between about 25° C and 100° C. In practice, the 4-hydroxy-1,2-dialkyl-3,5-disubstituted pyrazolium salt is initially treated with an alkali metal hydroxide or $C_1$-$C_4$ alkali metal alkoxide, preferably sodium or potassium hydroxide or sodium or potassium methoxide, in the presence of an aprotic solvent at an elevated temperature, e.g. 50° C to 80° C; then cooled and thereafter treated with an alkylating agent as described above.

A number of intermediate pyrazoles of type II can be prepared by variations of known procedures such as those reported by Nye and Tang, Tetrahedron 28: 455-462 (1972), or Arbuzov et al., Bull. Acad. Sci. USSR 22: 1388 (1973). Other pyrazoles of type II may be prepared by a variety of procedures set forth and/or exemplified hereinbelow.

Intermediate pyrazoles of type II, wherein the bridge between the pyrazole ring and the rest of the $R_4$ group is sulfur can be prepared using a procedure described by R. Adams and A. Feretti, Journal of the American Chemical Society 81; 4927 (1959), employing the appropriate cuprous mercaptide and reacting with the appropriate 4-bromopyrazole in quinoline.

Conversion of the formula I pyrazolium salt:

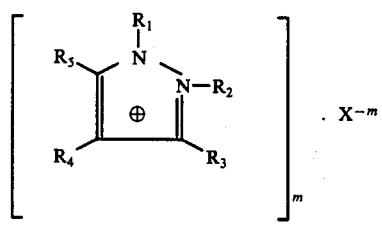

wherein $R_4$ is a member selected from the group consisting of alkylthio $C_1$-$C_{22}$ straight chain or branched, the moiety: $-O(CH_2)_n-W$, where $n$ is an integer selected from 1, 2, 3 and 4, and W is a member selected from alkylthio $C_1$-$C_7$ straight chain or branched and benzylthio,

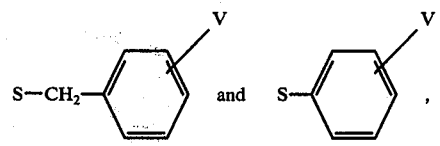

where V is a member selected from the group consisting of hydrogen, halogen, alkyl $C_1$-$C_4$ straight chain or branched, alkoxy $C_1$-$C_4$ straight chain or branched, $NO_2$ and $CF_3$; and $R_1$, $R_2$, $R_3$, $R_5$, X and $m$ are as defined above, to the corresponding formula I pyrazolium salt wherein $R_4$ is alkyl sulfonyl $C_1$-$C_{22}$, the moiety: $-O(CH_2)_n-W$ where $n$ is selected from 1, 2, 3 and 4, and W is selected from alkyl sulfonyl $C_1$-$C_7$ straight chain or branched, benzyl sulfonyl,

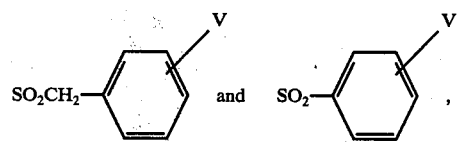

where V is as hereinabove defined; and $R_1$, $R_2$, $R_3$, $R_5$, X and $m$ are as defined above, can be achieved by the oxidation of the said formula I thio compounds with m-chloroperbenzoic acid in chloroform at a temperature between about 40° C and 70° C.

Among the compounds of the present invention which are preferred and are prepared by one or more of the above-identified methods of synthesis are:

4-Methoxy-1,2-dimethyl-3,5-diphenylpyrazolium perchlorate;
4-Methoxy-1,2-dimethyl-3,5-diphenylpyrazolium bromide;
4-Methoxy-1,2-dimethyl-3,5-diphenylpyrazolium iodide;
4-Methoxy-1,2-dimethyl-3,5-diphenylpyrazolium methyl sulfate;
4-Ethoxy-1,2-dimethyl-3,5-diphenylpyrazolium perchlorate;
1,2-Dimethyl-3,5-diphenyl-4-n-propoxypyrazolium methyl sulfate;
4-Allyloxy-1,2-dimethyl-3,5-diphenylpyrazolium perchlorate;
1,2-Dimethyl-3,5-diphenyl-4-(2-propynyloxy)-pyrazolium perchlorate;
4-Benzyloxy-1,2-dimethyl-3,5-diphenylpyrazolium methyl sulfate;
1-Ethyl-4-methoxy-2-methyl-3,5-diphenylpyrazolium perchlorate;
4-Methoxy-1-methyl-3,5-diphenyl-2-n-propyl-pyrazolium perchlorate;
3-(p-Chlorophenyl)-4-methoxy-1,2-dimethyl-5-phenylpyrazolium methyl sulfate;
3,5-(Di-p-chlorophenyl)-4-methoxy-1,2-dimethyl-pyrazolium perchlorate;
1,2-Dimethyl-3,5-diphenyl-4-n-dodecyloxypyrazolium methyl sulfate;
1,2-Dimethyl-3,5-diphenyl-4-methyleneoxyethoxypyrazolium chloride;

1,2-Dimethyl-3,5-diphenyl-4-methyleneoxyethylthiopyrazolium phosphate;
3,5-Diphenyl-1-ethyl-2-methyl-4-phenoxypyrazolium methyl sulfate;
3,5-Diphenyl-1-ethyl-4-isopropylthio-2-methylpyrazolium chloride;
4-Benzylthio-1,2-dimethyl-3,5-diphenylpyrazolium tetrafluoroborate;
4-Benzylsulfonyl-1,2-dimethyl-3,5-diphenylpyrazolium tetrafluoroborate;
4-(Chloroallyloxy)-1,2-dimethyl-3,5-diphenylpyrazolium methyl sulfate;
1,2-Dimethyl-3,5-diphenyl-4-(3-trifluoromethylbenzyloxy)-pyrazolium perchlorate;
4-Methoxy-1,2-dimethyl-3,5-(di-o-tolyl)pyrazolium iodide;
4-Methoxy-1,2-dimethyl-3-phenyl-5-(m-tolyl)-pyrazolium hydrogen sulfate;
3-(p-Fluorophenyl)-4-methoxy-1,2-dimethyl-5-phenylpyrazolium sulfate;
3-(p-Anisyl)-4-methoxy-1,2-dimethyl-5-phenylpyrazolium chloride;
4-Hexadecyloxy-1,2-dimethyl-3,5-diphenylpyrazolium methyl sulfate;
1,2-Dimethyl-4-methylthio-3,5-diphenylpyrazolium perchlorate;
1,2-Dimethyl-4-methylsulfonyl-3,5-diphenylpyrazolium perchlorate; and
1,2-Dimethyl-3,5-diphenyl-4-(2-propynyloxy)-pyrazolium methyl sulfate.

As indicated above, the compounds of this invention are highly effective herbicidal agents. They are effective for the control of many broadleaf weeds and grass weeds and differ in biological activity from the 1,2-dialkyl-3,5-diphenylpyrazolium salts which are not substituted in the 4-position of the pyrazolium ring. They differ in their superior effectiveness for control of broadleaf weeds such as Sesbania, mustard, pigweed and morningglory and of grass weeds such as barnyardgrass, crabgrass and foxtail, and are generally highly selective for the control of grass weeds in the presence of rice. However, they are less effective than the pyrazolium compounds of the above-referred-to Klingsberg et al. Netherlands Application as wild oat herbicidal agents.

In practice, it is found that the compounds of this invention are generally most effective when applied to the foliage of undesirable plants at rates between about 0.25 and 10 pounds per acre, calculated as the cation.

Advantageously, many of the formula (I) pyrazolium salts demonstrate a high degree of water solubility and lend themselves to dissolution in situ, or to the preparation of aqueous concentrates. Among the preferred salts in this regard are the methyl sulfates, hydrogen sulfates, sulfates, chlorides and bromides. In practice, the aqueous concentrates may be applied directly as a liquid spray to the foliage of undesirable plants or they may be further diluted with water and applied as dilute aqueous sprays to said undesirable plants.

Water-miscible concentrates are prepared by dissolving from 15% to 95% of the compound in 85% to 5% of a water-miscible solvent, such as water itself or another polar water-miscible solvent such as 2-methoxyethanol, methanol, propylene glycol, diethylene glycol, diethylene glycol monoethyl ether, formamide and dimethylformamide. Application of the material is made by adding a predetermined quantity of the water-miscible concentrate to a spray tank and applying the mixture as such or in combination with a suitable diluent such as a further quantity of water or one of the above polar solvents. Generally, addition of a surfactant to the mixture is also desirable.

The surfactant is preferably a nonionic surfactant such as an alkylphenol ethylene oxide condensate, and is used at the level of about 0.17% to 5% by volume.

Herbicidal concentrates containing surfactants can be formulated as aqueous sprays containing approximately 30% by weight of the appropriate salt, from about 25% to 50% by weight of water and the remainder of said formulation (20% to 45% by weight) of a selected surfactant.

Other formulations which may be prepared with the compounds of this invention include dusts, dust concentrates and wettable powders.

Dusts are generally prepared by grinding together about 1% to 25% by weight of the active agent with from about 99% to 75% by weight of a solid diluent such as kaolin, attapulgite, diatomaceous earth, or the like. Dust concentrates are prepared in similar fashion excepting that about 25% to 95% by weight of the active compound is ground with about 75% to 5% by weight of the diluent.

Wettable powders are prepared in the same manner as the dust concentrates excepting what about 1% to 5% by weight of a dispersing agent such as sodium lignosulfonate, or the sodium salt of condensed naphthalene sulfonic acid is blended with the mixture and about 1% to 5% of a surfactant is also blended with the formulation.

In practice, the wettable powder is dispersed in water and applied as a liquid spray to the foliage of undesirable plants. Application rates should be sufficient to provide about 0.25 to 10 pounds per acre of the pyrazolium cation, although 0.5 to 5 pounds per acre of said cation is generally satisfactory to control undesirable broadleaf weeds and undesirable grass plants.

This invention is further illustrated by the examples set forth below.

EXAMPLE 1

Preparation of 4-Methoxy-1,2-dimethyl-3,5-diphenylpyrazolium perchlorate.

Method A

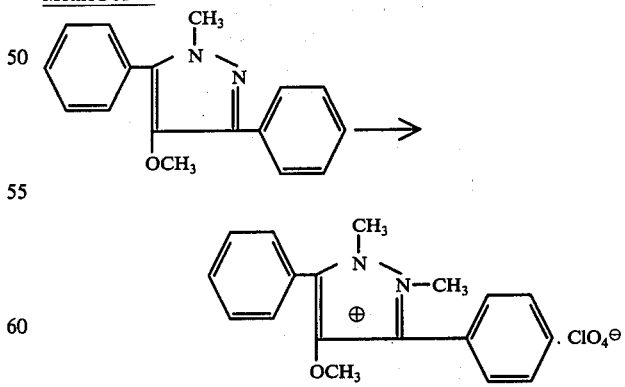

4-Methoxy-1-methyl-3,5-diphenylpyrazole (2.5 g, 0.0095 mole) in molecular sieve-dried toluene (80 ml) is heated to 50° C and dimethyl sulfate (2.5 g, 0.02 mole) is added. The mixture is stirred and heated under reflux for 6 hours, cooled and set aside overnight. Water (100 ml) is then added and this aqueous layer separated and treated with 10% aqueous perchloric acid. After 30 minutes, 0.6 g (16%) of a white powder is filtered off with a melting point of 135°–136° C.

Analysis calculation for $C_{18}H_{19}N_2ClO_5$: C, 57.05; H, 5.06; N, 7.40. Found: C, 56.96; H, 5.17; N, 7.40.

EXAMPLE 2

Preparation of 4-Methoxy-1,2-dimethyl-3,5-diphenylpyrazolium perchlorate.

Method B

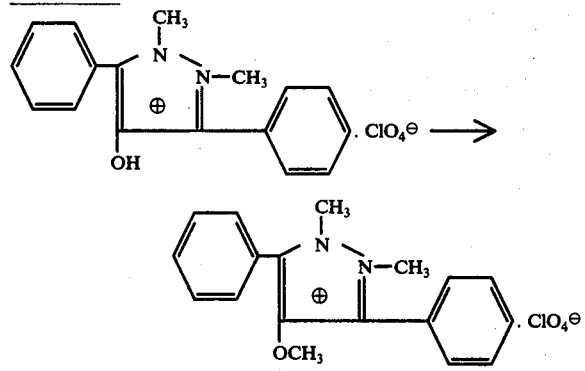

4-Hydroxy-1,2-dimethyl-3,5-diphenylpyrazolium perchlorate (7 g, 0.02 mole) in DMSO (2.5 ml) is added to 5% sodium hydroxide (0.84 g, 0.02 mole) in DMSO (100 ml), dropwise with stirring. The mixture is warmed to 60° C for 5 minutes, then stirred at room temperature for 4 hours. The reaction mixture (75 ml) is treated with methyl iodide (0.43 g, 0.013 mole) and the mixture is stirred at room temperature for 16 hours, then heated at 40° C for 2 hours. On pouring into water, a solid precipitates with melting point 88° C. One crystallization from methanol gives the product with melting point 132°–132.5° C in 53% yield.

EXAMPLE 3

Preparation of 4-Methoxy-1,2-dimethyl-3,5-diphenylpyrazolium methyl sulfate.

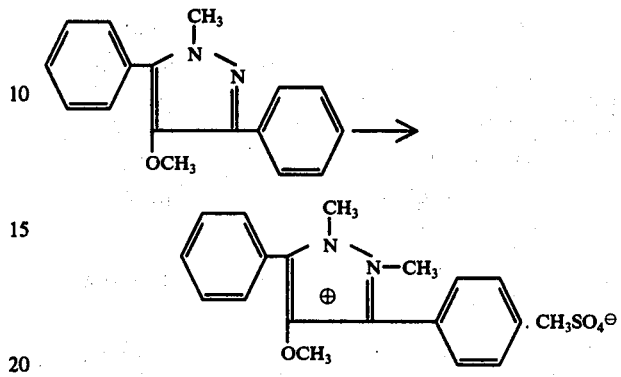

4-Methoxy-1-methyl-3,5-diphenylpyrazole (20 g, 0.076 mole) is suspended in dimethyl sulfate (23 g) at 20° C and the mixture is stirred and the reaction temperature raised to 130° C. At 70° C the mixture becomes a homogeneous solution and at 130° C some darkening occurs. After maintaining the reaction at 130° C for 1 hour, it is cooled and the mixture poured into toluene (250 ml). The toluene layer is decanted off and further toluene is added, decanted off, and this sequence repeated a third time. The residual oil, obtained from the above treatment, is then treated with acetone (10 ml) which has been dried over anhydrous potassium carbonate. This yields a crystalline product which is filtered off and washed with ether. The acetone filtrate is evaporated to give 27.5 g of oil, dissolved in water, and extracted with chloroform. The chloroform layer is evaporated to a small volume and then ether added. A white precipitate is obtained; combined yield 22 g (74%) of melting point 104.5°–105° C is obtained.

EXAMPLE 4

Compounds of the present invention are prepared in accordance with the procedure of Examples 1 or 2 above with appropriate substitution of reactants. Compounds prepared are listed in Table I below, with identification of process used, reagent, yield where determined and characterization of product obtained.

TABLE I

| Preparation and Properties of Pyrazolium Salts Represented by Formula (I) | | | | | | | |
|---|---|---|---|---|---|---|---|
| Compound | Method | Reagent | % Yield | Melting Point °C | Analysis | Calculated | Found |
| 4-Methoxy-1,2-dimethyl-3,5-diphenylpyrazolium bromide | A | $(CH_3)_2SO_4$, aq. HBr | 57 | 163–164 | C, H, N, | 60.18 5.33 7.80 | 59.83 5.41 7.71 |
| 4-Methoxy-1,2-dimethyl-3,5-diphenylpyrazolium iodide | A | $(CH_3)_2SO_4$, aq. HBr | 78 | 167–168 | C, H, N, | 53.22 4.71 6.90 | 53.27 4.85 6.93 |
| 4-Methoxy-1,2-dimethyl-3,5-diphenylpyrazolium methyl sulfate | A | $(CH_3)_2SO_4$ | 74 | 104–105 | C, H, N, | 58.45 5.68 7.17 | 58.62 5.77 7.22 |
| 4-Ethoxy-1,2-dimethyl-3,5-diphenylpyrazolium perchlorate | B | $C_2H_5I$/NaH/DMF | 29 | 91–93 | C, H, N, | 58.09 5.39 7.13 | 57.86 5.43 7.03 |
| 1,2-Dimethyl-3,5-diphenyl-4-n-propoxypyrazolium perchlorate | A | $(CH_3)_2SO_4$, aq. $HClO_4$ | 70 | 104–105 | C, H, N, | 59.03 5.07 6.89 | 58.96 5.76 6.79 |
| 4-Allyloxy-1,2-dimethyl-3,5-diphenylpyrazolium perchlorate | A | $(CH_3)_2SO_4$, aq. $HClO_4$ | 70 | 105–107 | C, H, N, | 59.30 5.22 6.92 | 59.24 5.24 6.82 |
| 1,2-Dimethyl-3,5-diphenyl-4-(2-propynyloxy)pyrazolium perchlorate | A | $(CH_3)_2SO_4$, aq. $HClO_4$ | — | 136–137 | C, H, N, | 59.63 4.75 6.95 | 59.61 4.84 6.75 |

TABLE I-continued
Preparation and Properties of Pyrazolium Salts Represented by Formula (I)

| Compound | Method | Reagent | % Yield | Melting Point °C | Analysis Calculated | Found |
|---|---|---|---|---|---|---|
| 1,2-Dimethyl-3,5-diphenyl-4-(2-propynyloxy)pyrazolium methyl sulfate | A | $(CH_3)_2SO_4$ Toluene | 26 | 154–155 | C, 60.86<br>H, 5.35<br>N, 6.76<br>S, 7.74 | 61.62<br>5.35<br>6.75<br>7.57 |
| 1-Ethyl-4-methoxy-2-methyl-3,5-diphenylpyrazolium perchlorate | A | $(C_2H_5)_2SO_4$, aq. $HClO_4$ | — | 148–149 | C, 58.09<br>H, 5.38<br>N, 7.13 | 58.03<br>5.40<br>7.17 |
| 4-Methoxy-1-methyl-3,5-diphenyl-2-n-propyl-pyrazolium perchlorate, ½ $H_2O$ | A | $(n-C_3H_7)_2SO_4$, aq. $HClO_4$ | 53 | 108.5–108.7 | C, 57.76<br>H, 5.82<br>N, 6.74 | 57.96<br>5.74<br>6.30 |
| 1-Ethyl-4-methoxy-2-methyl-3,5-diphenylpyrazolium ethyl sulfate | A | $(C_2H_5)_2SO_4$ | 66 | — | C, 60.27<br>H, 6.26<br>N, 6.69<br>S, 7.66 | 58.65<br>6.35<br>6.48<br>7.40 |
| 4-Isobutoxy-1,2-dimethyl-3,5-diphenylpyrazolium methyl sulfate | A | $(CH_3)_2SO_4$ | 93 | 89–90 | C, 61.10<br>H, 6.53<br>N, 6.48<br>S, 7.40 | 61.55<br>6.68<br>6.57<br>7.70 |
| 4-Hexyloxy-1,2-dimethyl-3,5-diphenylpyrazolium methyl sulfate | A | $(CH_3)_2SO_4$ | 53 | 64–65 | C, 62.59<br>H, 7.00<br>N, 6.08<br>S, 6.95 | 62.11<br>6.77<br>5.70<br>6.41 |
| 4-Heptyloxy-1,2-dimethyl-3,5-diphenylpyrazolium methyl sulfate | A | $(CH_3)_2SO_4$ | 83 | — | C, 63.27<br>H, 7.22<br>N, 5.90<br>S, 6.72 | 63.21<br>7.42<br>5.42<br>6.43 |
| 1,2-Dimethyl-3,5-diphenyl-4-octyloxypyrazolium methyl sulfate | A | $(CH_3)_2SO_4$ | 39 | — | C, 63.91<br>H, 7.43<br>N, 5.73<br>S, 6.55 | 64.73<br>7.30<br>5.70<br>6.53 |
| 4-Decyloxy-1,2-dimethyl-3,5-diphenylpyrazolium methyl sulfate | A | $(CH_3)_2SO_4 \cdot H_2O$ | 58 | — | C, 62.90<br>H, 7.92<br>N, 5.24<br>S, 5.98 | 61.28<br>7.65<br>5.12<br>5.78 |
| 1,2-Dimethyl-3,5-diphenyl-4-tridecyloxypyrazolium methyl sulfate | A | $(CH_3)_2SO_4$ | 80 | — | C, 66.64<br>H, 8.30<br>N, 5.01<br>S, 5.73 | 66.22<br>8.41<br>5.09<br>5.76 |
| 4-Hexadecyloxy-1,2-dimethyl-3,5-diphenylpyrazolium methyl sulfate | A | $(CH_3)_2SO_4$ | 71 | — | C, 67.97<br>H, 8.72<br>N, 4.66<br>S, 5.37 | 67.21<br>8.76<br>4.19<br>5.06 |
| 4-[(Cyclohexylmethyl)oxy]-1,2-dimethyl-3,5-diphenyl-pyrazolium methyl sulfate | A | $(CH_3)_2SO_4$ | 43 | — | C, 63.54<br>H, 6.83<br>N, 5.93<br>S, 6.77 | 65.31<br>6.56<br>4.97<br>5.36 |
| 4-(2-Chloroallyloxy)-1,2-dimethyl-3,5-diphenyl-pyrazolium methyl sulfate | A | $(CH_3)_2SO_4$ | 36 | — | C, 55.93<br>H, 5.14<br>N, 6.21<br>S, 7.11<br>Cl, 7.86 | 52.67<br>5.13<br>6.02<br>7.34<br>8.06 |
| 4-(3-Chloroallyloxy)-1,2-dimethyl-3,5-diphenyl-pyrazolium methyl sulfate | A | $(CH_3)_2SO_4$ | 86 | — | C, 55.93<br>H, 5.14<br>N, 6.21<br>S, 7.11<br>Cl, 7.86 | 55.95<br>5.55<br>6.08<br>6.83<br>8.06 |
| 1,2-Dimethyl-4-(octadecyl-oxy)-3,5-diphenyl-pyrazolium methyl sulfate | A | $(CH_3)_2SO_4$ | 27 | wax | C, 68.76<br>H, 8.98<br>N, 4.46<br>S, 5.09 | 68.46<br>8.61<br>4.56<br>5.20 |
| 4-[2-(Heptyloxy)ethoxy]-1,2-dimethyl-3,5-diphenyl-pyrazolium methyl sulfate | A | $(CH_3)_2SO_4$ | 55 | — | C, 60.43<br>H, 7.51<br>N, 5.22<br>S, 5.96 | 60.07<br>6.97<br>5.10<br>5.72 |
| 4-(2-Bromoethoxy)-1,2-dimethyl-3,5-diphenyl-pyrazolium methyl sulfate | A | $(CH_3)_2SO_4$ | 78 | 97–98 | C, 49.69<br>H, 4.79<br>N, 5.74<br>S, 6.63<br>Br, 16.53 | 50.43<br>4.95<br>5.74<br>6.46<br>15.98 |
| 4-(2-Iodoethoxy)-1,2-dimethyl-3,5-diphenyl-pyrazolium methyl sulfate | A | $(CH_3)_2SO_4$ | 79 | 94–95 | C, 45.29<br>H, 4.37<br>N, 5.28<br>S, 6.05<br>I, 23.93 | 45.60<br>4.27<br>5.66<br>6.12<br>25.09 |
| 4-[2-(Benzylsulfonyl)ethoxy]-1,2-dimethyl-3,5-diphenyl-pyrazolium methyl sulfate | A | $(CH_3)_2SO_4$ | 50 | 123 | C, 58.04<br>H, 5.41<br>N, 5.1<br>S, 11.47 | 58.21<br>5.67<br>5.93<br>10.28 |
| 1,2-Dimethyl-4-[2-(methyl-thio)ethoxy]-3,5-diphenyl-pyrazolium methyl sulfate | A | $(CH_3)_2SO_4$ Toluene | 20 | 159.5–161 | C, 51.51<br>H, 4.97<br>N, 6.01<br>S, 6.88<br>I, 27.21 | 50.07<br>4.90<br>5.94<br>5.84<br>28.76 |
| 4-(Butylthio)-1,2-dimethyl-3,5-diphenylpyrazolium methyl sulfate | A | $(CH_3)_2SO_4$/Benzene | 49 | syrup | C, 58.92<br>H, 6.29<br>N, 6.25<br>S, 14.27 | 58.62<br>6.51<br>6.28<br>14.04 |
| 4-(Butylthio)-1,2-dimethyl- | A | $(CH_3)_2SO_4$ | — | 137–138 | C, 54.30 | 54.35 |

TABLE I-continued

Preparation and Properties of Pyrazolium Salts Represented by Formula (I)

| Compound | Method | Reagent | % Yield | Melting Point °C | Analysis Calculated | Found |
|---|---|---|---|---|---|---|
| 3,5-diphenylpyrazolium iodide | | aq. KI | | | H, 5.43<br>N, 6.03<br>S, 6.90<br>I, 27.32 | 5.09<br>5.98<br>6.78<br>27.70 |
| 4-(Butylsulfonyl)-1,2-dimethyl-3,5-diphenyl-pyrazolium methyl sulfate | A | $(CH_3)_2SO_4$ | 76 | 164–168 | C, 54.99<br>H, 5.87<br>N, 5.83<br>S, 13.32 | 55.08<br>6.22<br>5.93<br>13.23 |
| 4-(Phenylthio)-1,2-dimethyl-3,5-diphenylpyrazolium methyl sulfate | A | $(CH_3)_2SO_4$ | 32 | 171–171.5 | C, 61.53<br>H, 5.16<br>N, 5.98<br>S, 13.66 | 61.76<br>4.90<br>5.91<br>13.90 |
| 4-(Phenylsulfonyl)-1,2-dimethyl-3,5-diphenyl-pyrazolium methyl sulfate | A | $(CH_3)_2SO_4$ | 30 | 185–186 | C, 57.60<br>H, 4.83<br>N, 5.60<br>S, 12.79 | 57.91<br>4.60<br>5.69<br>12.99 |
| 4-Propoxy-1,2-dimethyl-3,5-diphenylpyrazolium methyl sulfate | A | $(CH_3)_2SO_4$ | 90 | | C, 58.16<br>H, 6.47<br>N, 6.42<br>S, 7.35<br>(1 $H_2O$) | 58.16<br>6.20<br>6.29<br>7.62 |
| 4-Propoxy-1,2-dimethyl-3,5-diphenylpyrazolium chloride | A | $(CH_3)_2SO_4$,<br>Dowex 1-X8<br>(Ionic Form Cl⊖ | — | Hygroscopic solid | C, 70.07<br>H, 6.76<br>N, 8.17<br>Cl, 10.34 | 59.83<br>5.09<br>6.10<br>23.08 |
| 4-Propoxy-1,2-dimethyl-3,5-diphenylpyrazolium bromide | A | $(CH_3)_2SO_4$,<br>HBr | — | — | C, 62.02<br>H, 5.99<br>N, 7.24<br>Br, 20.64 | 61.45<br>6.28<br>7.14<br>20.31 |
| 4-Propoxy-1,2-dimethyl-3,5-diphenylpyrazolium iodide | A | $(CH_3)_2SO_4$,<br>KI | — | 140–141 | C, 55.31<br>H, 5.34<br>N, 6.45<br>I, 29.33 | 54.96<br>5.26<br>6.45<br>29.49 |
| 4-Isopropoxy-1,2-dimethyl-3,5-diphenylpyrazolium methyl sulfate | A | $(CH_3)_2SO_4$ | 95 | 95–98 | C, 57.78<br>H, 6.47<br>N, 6.42<br>S, 7.35<br>(1 $H_2O$) | 58.09<br>6.15<br>6.30<br>7.80 |
| 4-Isopropoxy-1,2-dimethyl-3,5-diphenylpyrazolium perchlorate | A | $(CH_3)_2SO_4$<br>$HClO_4$ | — | 45–147 | C, 59.03<br>H, 5.70<br>N, 6.89<br>Cl, 8.72 | 59.01<br>5.68<br>6.82<br>8.74 |
| 4-Butoxy-1,2-dimethyl-3,5-diphenylpyrazolium methyl sulfate | A | $(CH_3)_2SO_4$ | 73 | — | C, 61.10<br>H, 6.53<br>N, 6.48<br>S, 7.45 | 60.96<br>6.48<br>6.38<br>7.21 |
| 4-Butoxy-1,2-dimethyl-3,5-diphenylpyrazolium perchlorate | A | $(CH_3)_2SO_4$,<br>$HClO_4$ | — | 124–125 | C, 59.94<br>H, 5.99<br>N, 6.82<br>Cl, 8.42 | 60.28<br>5.93<br>6.73<br>8.38 |
| 4-sec-Butoxy-1,2-dimethyl-3,5-diphenylpyrazolium methyl sulfate | A | $(CH_3)_2SO_4$ | 81 | 109–110 | C, 61.10<br>H, 6.53<br>N, 6.48<br>S, 7.41 | 61.58<br>6.55<br>6.35<br>7.33 |
| 4-sec-Butoxy-1,2-dimethyl-I 3,5-diphenylpyrazolium perchlorate | A | $(CH_3)_2SO_4$<br>$NClO_4$ | — | 149–150 | C, 59.94<br>H, 5.99<br>N, 6.66<br>Cl, 8.43 | 59.95<br>5.93<br>6.65<br>8.51 |
| 4-Pentoxy-1,2-dimethyl-3,5-diphenylpyrazolium methyl sulfate | A | $(CH_3)_2SO_4$ | 66 | — | C, 60.63<br>H, 6.86<br>N, 6.15<br>S, 7.04<br>(½ $H_2O$) | 60.76<br>6.89<br>5.99<br>6.97 |
| 4-Pentoxy-1,2-dimethyl-3,5-diphenylpyrazolium perchlorate | A | $(CH_3)_2SO_4$,<br>$HClO_4$ | — | 86–87 | C, 60.75<br>H, 6.26<br>N, 6.44<br>Cl, 8.15 | 60.46<br>6.18<br>6.25<br>8.12 |
| 4-(o-Chlorobenzyloxy)-1,2-dimethyl-3,5-diphenyl-pyrazolium methyl sulfate | A | $(CH_3)_2SO_4$ | 62.6 | 95–98 | C, 59.94<br>H, 5.03<br>N, 5.59<br>S, 6.40<br>Cl, 7.08 | 59.84<br>4.96<br>5.71<br>6.32<br>8.68 |
| 4-(m-Chlorobenzyloxy)-1,2-dimethyl-3,5-diphenyl-pyrazolium methyl sulfate | A | $(CH_3)_2SO_4$ | 90.7 | 77–79 | C, 59.94<br>H, 5.03<br>N, 5.59<br>S, 6.40<br>Cl, 7.08 | 59.62<br>4.94<br>5.69<br>6.18<br>7.05 |
| 4-(p-Chlorobenzyloxy)-1,2-dimethyl-3,5-diphenyl-pyrazolium methyl sulfate | A | $(CH_3)_2SO_4$ | 78.3 | — | C, 57.85<br>H, 5.25<br>N, 5.28<br>S, 6.18<br>Cl, 6.83<br>(1 $H_2$) | 56.93<br>4.98<br>5.21<br>6.02<br>13.37<br>trace of $CHCl_3$ |
| 4-(p-Chlorobenzyloxy)-1,2-dimethyl-3,5-diphenyl-pyrazolium perchlorate | A | $(CH_3)_2SO_4$,<br>$HClO_4$ | | 128–130 | C, 58.90<br>H, 4.53<br>N, 5.73<br>Cl, 14.49 | 59.53<br>4.65<br>5.73<br>14.78 |

TABLE I-continued
Preparation and Properties of Pyrazolium Salts Represented by Formula (I)

| Compound | Method | Reagent | % Yield | Melting Point ° C | Analysis Calculated | Found |
|---|---|---|---|---|---|---|
| 4-(2,6-Dichlorobenzyloxy)-1,2-dimethyl-3,5-diphenyl-pyrazolium methyl sulfate | A | $(CH_3)_2SO_4$ | 74.2 | 189–190 | C, 56.08<br>H, 4.52<br>N, 5.23<br>S, 5.99<br>Cl, 13.24 | 55.40<br>4.62<br>5.19<br>6.20<br>13.84 |
| 4-(3,4-Dichlorobenzyloxy)-1,2-dimethyl-3,5-diphenyl-pyrazolium methyl sulfate | A | $(CH_3)_2SO_4$ | 63 | 77–85 | C, 53.87<br>H, 4.45<br>4.34<br>N, 5.03<br>S, 5.75<br>Cl, 13.72<br>($H_2O$) | 54.22<br><br><br>4.97<br>5.96<br>15.77 |
| 4-(p-Methylbenzyloxy)-1,2-dimethyl-3,5-diphenyl-pyrazolium methyl sulfate | A | $(CH_3)_2SO_4$ | 70.7 | 105–108 | C, 64.99<br>H, 5.87<br>N, 5.83<br>S, 6.67 | 63.92<br>6.06<br>5.83<br>6.77 |
| 4-(p-Bromobenzyloxy)-1,2-dimethyl-3,5-diphenyl-pyrazolium methyl sulfate | A | $(CH_3)_2SO_4$ | 89.9 | 73–79 | C, 54.64<br>H, 4.59<br>N, 5.10<br>S, 5.83<br>Br, 14.54 | 52.72<br>4.73<br>4.95<br>6.27<br>13.20 |
| 4-(p-Bromobenzyloxy)-1,2-dimethyl-3,5-diphenyl-pyrazolium perchlorate | A | $(CH_3)_2SO_4$, $HClO_4$ | — | 156–158 | C, 54.01<br>H, 4.16<br>N, 5.25<br>Br, 14.97<br>Cl, 6.64 | 53.79<br>4.08<br>5.13<br>15.11<br>6.43 |
| 4-(p-Methoxybenzyloxy)-1,2-dimethyl-3,5-diphenyl-pyrazolium methyl sulfate | A | $(CH_3)_2SO_4$ | 78.4 | 105–107 | C, 62.87<br>H, 5.68<br>N, 5.64<br>S, 6.46 | 61.90<br>5.68<br>5.57<br>6.56 |
| 4-(p-tert-Butylbenzyloxy)-1,2-dimethyl-3,5-diphenyl-pyrazolium methyl sulfate | A | $(CH_3)_2SO_4$ | 77.6 | 111–115 | C, 65.51<br>H, 6.64<br>N, 5.27<br>S, 6.03<br>(½ $H_2O$) | 65.60<br>7.14<br>5.43<br>6.31 |
| 1,2-Dimethyl-3,5-diphenyl-4-{[m-(trifluoromethyl)-benzyl]oxy}pyrazolium methyl sulfate | A | $(CH_3)_2SO_4$ | 80 | — | C, 58.43<br>H, 4.72<br>N, 5.24<br>S, 6.00<br>F, 10.66 | 57.57<br>4.59<br>4.94<br>5.83<br>10.83 |
| 1,2-Dimethyl-3,5-diphenyl-4-{[m-(trifluoromethyl)-benzyl]oxy}pyrazolium perchlorate | A | $(CH_3)_2SO_4$, $HClO_4$ | — | 157–158 | C, 57.42<br>H, 4.24<br>N, 5.36<br>Cl, 6.78<br>F, 10.90 | 56.99<br>4.31<br>5.16<br>7.08<br>10.52 |
| 4-(m-Cyanobenzyloxy)-1,2-dimethyl-3,5-diphenyl-pyrazolium methyl sulfate | A | $(CH_3)_2SO_4$ | 85.9 | — | C, 61.27<br>H, 5.34<br>N, 8.25<br>S, 6.29<br>(1 $H_2O$) | 61.60<br>4.95<br>8.05<br>6.10 |
| 4-(m-Cyanobenzyloxy)-1,2-dimethyl-3,5-diphenyl-pyrazolium perchlorate | A | $(CH_3)_2SO_4$ $HClO_4$ | — | 114–115 | C, 62.57<br>H, 4.62<br>N, 8.76<br>Cl, 7.39 | 62.57<br>4.68<br>8.60<br>7.39 |
| 4-(p-Nitrobenzyloxy)-1,2-dimethyl-3,5-diphenyl-pyrazolium methyl sulfate | A | $(CH_3)_2SO_4$ | 81 | 128–129 | C, 58.71<br>H, 4.93<br>N, 8.22<br>S, 6.27 | 58.62<br>5.05<br>8.17<br>6.40 |
| 1,2-Dimethyl-4-(α-methyl-benzyloxy)-3,5-diphenyl-pyrazolium methyl sulfate | A | $(CH_3)_2SO_4$ | — | Hygroscopic solid | C, 60.40<br>H, 6.24<br>N, 5.42<br>S, 6.21<br>(2 $H_2O$) | 60.04<br>6.19<br>5.30<br>5.93 |
| 1,2-Dimethyl-4-(α-methyl-benzyloxy)-3,5-diphenyl-pyrazolium perchlorate | A | $(CH_3)_2SO_4$ $HClO_4$ | — | 166–167 | C, 64.05<br>H, 5.38<br>N, 5.98<br>Cl, 7.56 | 63.87<br>5.17<br>5.69<br>6.87 |
| 4-Diphenylmethoxy-1,2-dimethyl-3,5-diphenyl-pyrazolium methyl sulfate | A | $(CH_3)_2SO_4$ | — | 95–98 | C, 66.30<br>H, 5.74<br>N, 4.99<br>S, 5.71<br>($H_2O$) | 65.21<br>5.75<br>5.24<br>6.17 |
| 1,2-Dimethyl-4-(p-nitro-phenoxy)-3,5-diphenyl-pyrazolium methyl sulfate | A | $(CH_3)_2SO_4$ | 71 | 178–179 | C, 55.89<br>H, 4.89<br>S, 6.22<br>(1 $H_2O$) | 55.62<br>4.07<br>6.15 |
| 1,2-Dimethyl-4-(p-chloro-phenoxy)-3,5-diphenyl-pyrazolium methyl sulfate | A | $(CH_3)_2SO_4$ | 96.5 | 133–138 | N, 5.75<br>S, 6.59 | 5.05<br>5.89 |
| 1,2-Dimethyl-4-phenoxy-3,5-diphenylpyrazolium methyl sulfate | A | $(CH_3)_2SO_4$ | 27.3 | Hygroscopic solid | | |
| 1-Allyl-2-methyl-3,5-diphenyl-4-propoxypyrazolium methyl sulfate | A | (DMS) Benzene | 89 | oil | C, 59.72<br>H, 6.54<br>N, 6.06<br>S, 6.93<br>($H_2O$) | 58.64<br>6.50<br>6.34<br>7.19 |
| 4-Benzyloxy-1-methyl-2-pentyl-3,5-diphenylpyrazolium | A | DMS Xylene | 50 | oil | C, 64.42<br>H, 6.34 | 64.17<br>6.54 |

TABLE I-continued
Preparation and Properties of Pyrazolium Salts Represented by Formula (I)

| Compound | Method | Reagent | % Yield | Melting Point °C | Analysis Calculated | | Found |
|---|---|---|---|---|---|---|---|
| methyl sulfate | | | | | N, | 5.18 | 5.51 |
| | | | | | S, | 5.93 | 6.49 |
| 4-Benzyloxy-1,2-dimethyl-3,5-diphenylpyrazolium methyl sulfate | A | DMS Xylene | 78 | 131–132 | C, | 63.42 | 64.23 |
| | | | | | H, | 5.77 | 5.68 |
| | | | | | N, | 6.16 | 5.93 |
| 4-Benzyloxy-1,2-dimethyl-3,5-diphenylpyrazolium perchlorate | A | DMS aq. HClO$_4$ | — | 198–199 | C, | 63.37 | 63.52 |
| | | | | | H, | 5.10 | 5.26 |
| | | | | | N, | 6.16 | 6.07 |
| 4-Benzyloxy-1,2-dimethyl-3,5-diphenylpyrazolium tetrafluoroborate | A | DMS aq. NaBF$_4$ | — | 178–179.5 | C, | 65.18 | 65.28 |
| | | | | | H, | 5.24 | 5.30 |
| | | | | | N, | 6.33 | 6.37 |
| 4-Benzyloxy-3,5-diphenyl-1,2-diethylpyrazolium ethyl sulfate | A | Ethyl Sulfate (DES) Benzene | 31 | oil | C, | 63.86 | 62.60 |
| | | | | | H, | 6.50 | 6.18 |
| | | | | | N, | 5.32 | 5.50 |
| | | | | | S, | 6.09 | 6.36 |
| | | | | | | (H$_2$O) | |
| 4-Benzyloxy-3,5-diphenyl-1-ethyl-2-methylpyrazolium iodide | A | DMS Benzene | 45 | 148.5–150.0 | C, | 60.49 | 60.45 |
| | | | | | H, | 5.08 | 4.90 |
| | | | | | N, | 5.64 | 5.58 |
| | | | | | I, | 25.57 | 25.55 |
| 4-Benzyloxy-3,5-diphenyl-2-methyl-1-n-propyl-pyrazolium iodide | A | DMS aq. NaI | — | 106–138 (oil) | | | |
| 4-Benzyloxy-3,5-diphenyl-1-2-methyl-1-n-propyl-methyl sulfate | A | DMS Benzene | 65 | oil | C, | 65.57 | 65.40 |
| | | | | | H, | 6.11 | 6.05 |
| | | | | | N, | 5.67 | 5.72 |
| | | | | | S, | 6.48 | 6.44 |
| 1-Benzyl-4-methoxy-2-methyl-3,5-diphenylpyrazolium methyl sulfate | A | (CH$_3$)$_2$SO$_4$ | — | oil | C, | 61.98 | 61.92 |
| | | | | | H, | 5.83 | 5.99 |
| | | | | | N, | 5.78 | 5.48 |
| 1-Benzyl-4-methoxy-2-methyl-3,5-diphenylpyrazolium perchlorate | A | (CH$_3$)$_2$SO$_4$, HClO$_4$ | 28 | 165–166.5 | C, | 63.36 | 61.87 |
| | | | | | H, | 5.10 | 5.05 |
| | | | | | N, | 6.16 | 6.03 |
| 3,5-Diphenyl-1-methyl-4-methoxy-2-propylpyrazolium perchlorate | A | Dipropyl Sulfate HClO$_4$ | 49 | 108.5–108.7 | C, | 59.04 | 57.96 |
| | | | | | H, | 5.70 | 5.74 |
| | | | | | N, | 6.89 | 6.30 |
| 5-(p-Chlorophenyl)-1,2-dimethyl-3-phenyl-4-propoxypyrazolium methyl sulfate | A | (CH$_3$)$_2$SO$_4$ | 86 | 64–65 | C, | 55.68 | 55.39 |
| | | | | | H, | 5.56 | 5.89 |
| | | | | | N, | 6.19 | 6.05 |
| | | | | | S, | 7.08 | 7.08 |
| | | | | | Cl, | 7.83 | 7.76 |
| 5-(p-Chlorophenyl)-1,2-dimethyl-3-phenyl-4-propoxypyrazolium perchlorate | A | (CH$_3$)$_2$SO$_4$ HClO$_4$ | — | 147–148 | C, | 54.44 | 54.87 |
| | | | | | H, | 5.03 | 5.10 |
| | | | | | N, | 6.35 | 6.28 |
| | | | | | Cl, | 16.08 | 16.03 |
| 1,2-Dimethyl-4-propoxy-3,5-di-p-tolylpyrazolium tetrafluoroborate | A | (CH$_3$)$_2$SO$_4$, aq. NaBF$_4$ | — | 124.5–126.5 | C, | 62.58 | 62.49 |
| | | | | | H, | 6.45 | 6.67 |
| | | | | | N, | 6.63 | 6.59 |
| | | | | | F, | 17.99 | 17.82 |
| 1,2-Dimethyl-3-phenyl-4-propoxy-5-m-tolylpyrazolium methyl sulfate | A | (CH$_3$)$_2$SO$_4$ | 67 | 73–79 | C, | 61.09 | 61.34 |
| | | | | | H, | 6.52 | 6.48 |
| | | | | | N, | 6.48 | 6.44 |
| | | | | | S, | 7.41 | 7.60 |
| 3,5-bis(m-Chlorophenyl)-1,2-dimethyl-4-propoxy-pyrazolium methyl sulfate | A | (CH$_3$)$_2$SO$_4$ | 69 | 151.5–153.7 | C, | 51.75 | 51.65 |
| | | | | | H, | 4.96 | 4.64 |
| | | | | | N, | 5.75 | 5.64 |
| | | | | | S, | 6.56 | 6.69 |
| | | | | | Cl, | 14.55 | 14.83 |
| 1,2-Dimethyl-3-phenyl-4-propoxy-5-p-tolylpyrazolium methyl sulfate . ½ H$_2$O | A | (CH$_3$)$_2$SO$_4$ | 96 | Yellow Gum | C, | 59.85 | 60.15 |
| | | | | | H, | 6.62 | 6.42 |
| | | | | | N, | 6.34 | 6.17 |
| | | | | | S, | 7.26 | 7.13 |
| 1,2-Dimethyl-4-propoxy-3,5-di-m-tolylpyrazolium methyl sulfate | A | (CH$_3$)$_2$SO$_4$ | 79 | 91–93 | C, | 61.86 | 62.01 |
| | | | | | H, | 6.77 | 6.78 |
| | | | | | N, | 6.27 | 6.26 |
| | | | | | S, | 7.18 | 7.24 |
| 3-(p-Butoxyphenyl)-1,2-dimethyl-5-phenyl-4-propoxypyrazolium methyl sulfate . ¼ H$_2$O | A | (CH$_3$)$_2$SO$_4$ | 83 | Yellow Gum | C, | 60.65 | 60.36 |
| | | | | | H, | 7.02 | 6.71 |
| | | | | | N, | 5.66 | 5.83 |
| | | | | | S, | 6.48 | 6.79 |
| 1,2-Dimethyl-3-(2-naphthyl)-5-phenyl-4-propoxypyrazolium methyl sulfate, hydrated | A | (CH$_3$)$_2$SO$_4$ | 98 | Glass | C, | 62.88 | 62.84 |
| | | | | | H, | 6.12 | 6.15 |
| | | | | | N, | 5.86 | 5.90 |
| | | | | | S, | 6.71 | 6.89 |
| | | | | | (½ H$_2$O) | | |
| 3-(4-Biphenylyl)-1,2-dimethyl-5-phenyl-4-propoxypyrazolium methyl sulfate | A | (CH$_3$)$_2$SO$_4$ | 97 | Glass | C, | 65.56 | 65.40 |
| | | | | | H, | 6.11 | 6.13 |
| | | | | | N, | 5.66 | 5.41 |
| | | | | | S, | 6.48 | 6.28 |
| 3-o-Chlorophenyl-1,2-dimethyl-5-phenyl-4-propoxypyrazolium methyl sulfate, hydrated | A | (CH$_3$)$_2$SO$_4$ | 85 | Glass | C, | 55.68 | 55.33 |
| | | | | | H, | 5.56 | 5.55 |
| | | | | | N, | 6.18 | 5.91 |
| | | | | | S, | 7.08 | 6.72 |
| 1,2-Dimethyl-3-(p-dodecyl)-phenyl-5-phenyl-4-propoxy-pyrazolium methyl sulfate | A | (CH$_3$)$_2$SO$_4$ | | oil | | | |
| 3-(p-Chlorophenyl)-4-methoxy-1,2-dimethyl-5-phenyl- | A | (CH$_3$)$_2$SO$_4$ | 66.4 | 110–111 | C, | 53.70 | 55.89 |
| | | | | | H, | 4.98 | 5.43 |

TABLE I-continued
Preparation and Properties of Pyrazolium Salts Represented by Formula (I)

| Compound | Method | Reagent | % Yield | Melting Point °C | Analysis Calculated | Found |
|---|---|---|---|---|---|---|
| pyrazolium methyl sulfate | | | | | N, 6.60 | 6.03 |
| | | | | | S, 7.55 | 7.16 |
| | | | | | Cl, 8.34 | 7.86 |
| 3-(p-Chlorophenyl)-4-methoxy-1,2-dimethyl-5-phenyl-pyrazolium perchlorate | A | $(CH_3)_2SO_4$ HClO$_4$ | — | 76–78 | C, 52.30 | 52.53 |
| | | | | | H, 4.39 | 4.47 |
| | | | | | N, 6.78 | 6.67 |
| | | | | | Cl, 17.16 | 17.15 |

Additional exemplary matter is presented hereinbelow to illustrate and/or describe the preparation of the useful and novel pyrazoles, represented by the structure (II):

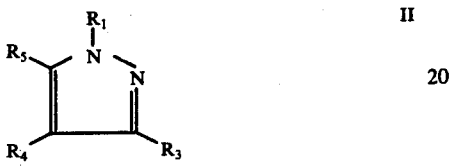

wherein $R_1$ represents a member selected from the group consisting of hydrogen, alkyl $C_1$–$C_5$, allyl and benzyl; $R_3$ represents a member selected from the group consisting of

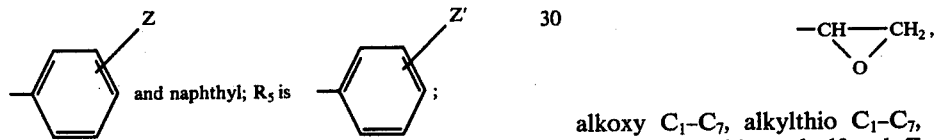

$R_4$ represents a member selected from the group consisting of alkoxy $C_1$–$C_{22}$, alkenyloxy $C_3$–$C_4$, halogen substituted alkenyloxy $C_3$–$C_4$, alkynyloxy $C_3$–$C_4$, —O—$(CH_2)_n$—W, alkylthio $C_1$–$C_{22}$, alkylsulfonyl $C_1$–$C_{22}$,

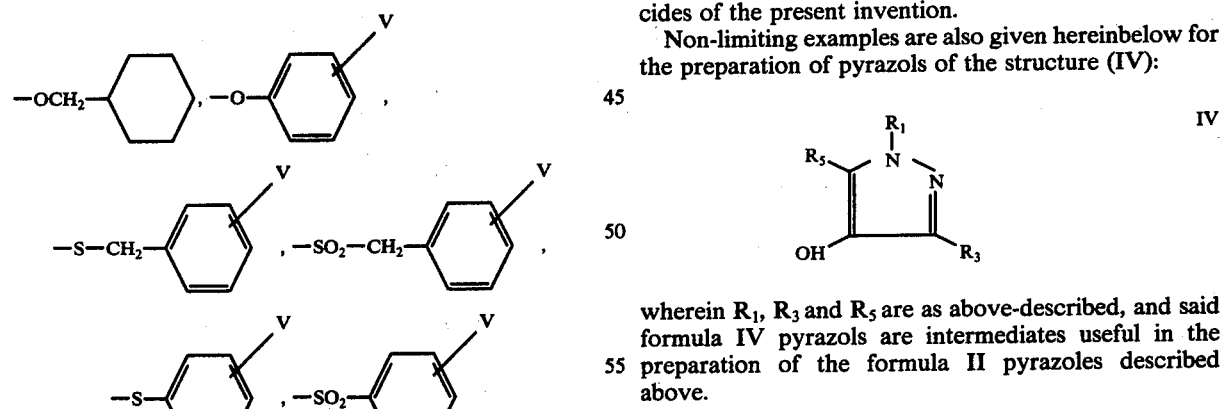

$R_6$ represents a member selected from the group consisting of hydrogen, methyl and phenyl; U and V each represent members selected from the group consisting of hydrogen, halogen, alkyl $C_1$–$C_4$, alkoxy $C_1$–$C_4$, $NO_2$ and $CF_3$; W represents a member selected from the group consisting of halogen, cyano, carbalkoxy $C_1$–$C_7$, $$-CH-CH_2,$$
$$\diagdown O \diagup$$

alkoxy $C_1$–$C_7$, alkylthio $C_1$–$C_7$, alkylsulfonyl $C_1$–$C_7$, benzylthio and benzylsulfonyl; Z and Z' each represent members selected from the group consisting of hydrogen, halogen, alkyl $C_1$–$C_{12}$, alkoxy $C_1$–$C_4$ and phenyl with the proviso that when $R_1$ is ethyl, $R_4$ cannot be ethoxy; $n$ is an integer selected from 1, 2, 3 and 4; said formula II pyrazoles being essential intermediates in the preparation of the novel formula I pyrazolium herbicides of the present invention.

Non-limiting examples are also given hereinbelow for the preparation of pyrazols of the structure (IV):

IV $R_5$—$\underset{\underset{OH}{|}}{C}$=$\underset{\underset{R_3}{|}}{N}$—$\overset{R_1}{\underset{|}{N}}$ wherein $R_1$, $R_3$ and $R_5$ are as above-described, and said formula IV pyrazols are intermediates useful in the preparation of the formula II pyrazoles described above.

EXAMPLE 5
General Method for Preparation of 4-Hydroxy-1-methyl-3,5-di(substituted-phenyl)-pyrazoles.

The procedure of M. J. Nye and W. P. Tang, Can. J. Chem. 51: 338 (1973), is followed. A mixture of 2-acetoxy-1,3-di(substituted-phenyl)-1,3-propanedione and methylhydrazine are allowed to react in n-propanol. Upon isolation of the product as described, the subject compounds are obtained. The compounds are listed in Table II below:

TABLE II

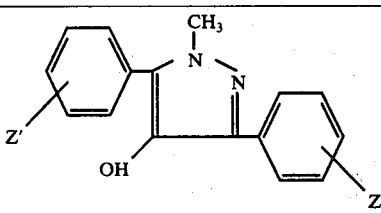

| Z | Z' | Melting Point °C |
|---|---|---|
| 2-chloro | H | 179–181 |
| 4-chloro | H | 128–132 |
| 3-chloro | 3-chloro | and 138.5 |
| 3-methyl | H | 131–135 |
| 4-methyl | H | 168–170 |
| 3-methyl | 3-methyl | 143–145 |
| 4-methyl | 4-methyl | 182–184 |
| 4-(n-dodecyl) | H | 96–106 |
| 4-(n-butoxy) | H | 152–170 |
| 4-phenyl | H | 185–201 |
|  |  | 158–173 |

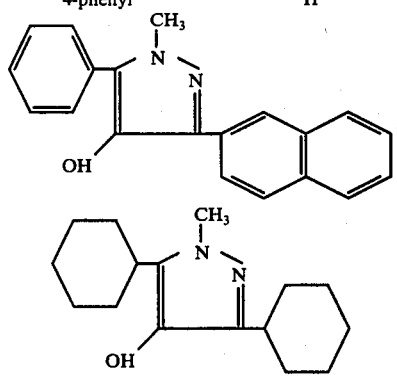

84–85

EXAMPLE 6

Preparation of 1-Benzyl-3,5-diphenyl-4-pyrazolol, acetate (ester).

Sodium acetate (5.13 g, 0.626 mole) is added to a mixture of 2-hydroxy-1,3-diphenyl-1,3-propanedione, acetate (8 g, 0.0283 mole), benzyl hydrazine dihydrochloride (6.1 g, 0.0313 mole) and 1-propanol (80 ml). The reaction mixture is stirred and heated slowly to 80° C. After heating for 2 hours, the mixture is poured into water. The solid formed, 11 g (105%), is isolated by filtration and recrystallized from methanol to give a white crystalline solid, melting poing 103°–103.5° C.

Analyses calculated for $C_{24}H_{20}N_2O_2$: C, 78.24; H, 5.47; N, 7.60. Found: C, 78.45; H, 5.66; N, 7.73.

EXAMPLE 7

Preparation of 1-Benzyl-3,5-diphenyl-4-pyrazolol.

A solution of sodium hydroxide (1.5 g, 0.0375 mole), methanol (30 ml) and water (30 ml) is added to 1-benzyl-3,5-diphenyl-4-pyrazolol, acetate (6.9 g, 0.019 mole) and the mixture stirred and refluxed for one hour. A white solid forms and is isolated by filtration, treated with dilute hydrochloric acid, washed with water and dried to give a white solid, 6.36 g, melting point 194°–195° C.

Analyses calculated for $C_{22}H_{18}N_2O$: C, 80.95; H, 5.56; N, 8.58. Found: C, 80.87; H, 5.67; N, 8.53.

EXAMPLE 8

General Methods for Preparation of 4-Alkoxy-1-methyl-3,5-diphenylpyrazoles and 3,5-di(substituted-phenyl)pyrazoles.

Method A

A mixture of 1-methyl-3,5-diphenyl-4-pyrazolol (0.04 mole) (or the appropriate substituted-phenyl pyrazole), benzyltriethylammonium chloride (1 g), the appropriate alkyl halide (0.08 mole) and aqueous sodium hydroxide (0.08 mole in 46 ml water) is stirred vigorously and heated at 60°–70° C for 24 hours. The reaction is followed by glc.

The cooled reaction mixture is extracted with methylene chloride. The methylene chloride layer is separated, washed with 10% aqueous sodium hydroxide solution, then washed well with water, dried (Drierite) and stripped in vacuo.

Method B

A mixture of 1-methyl-3,5-diphenyl-4-pyrazolol (0.06 mole), sodium methoxide (0.06 mole) and methanol (200 ml) is stirred and refluxed for 2 hours. The reaction mixture is then evaporated to dryness and azeotropically dried with toluene. The toluene is removed in vacuo and the residue dissolved in dry DMF (250 ml). The appropriate alkyl ester of p-toluenesulfonic acid (0.06 mole) is added, and the reaction mixture stirred overnight at room temperature. The reaction is followed by glc. The reaction mixture is heated at 50°–75° C as required to complete the reaction.

The cooled reaction mixture is poured into water and extracted with ether. The ether layer is separated, washed with 10% aqueous sodium hydroxide solution, washed well with water and then stripped in vacuo.

Method C

A mixture of 1-methyl-3,5-diphenyl-4-pyrazolol (0.02 mole), DMF (50 ml) and potassium t-butoxide or sodium methoxide (0.02 mole) is stirred and heated at 50° C for one hour. The appropriate aliphatic halide (0.04 mole) is added and the mixture heated at 55°–60° C for 2 to 3 hours.

The reaction mixture is poured into water and made alkaline with 1% aqueous sodium hydroxide solution. Crude solid products are isolated by filtration. In the case of oils, the products are isolated by extraction with chloroform. The chloroform layer is separated, washed with water and stripped in vacuo.

Compounds prepared by these methods are listed in Tables III and IV.

TABLE III

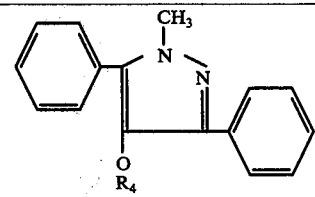

| $R_4$ | Melting Point °C | Method | Recrystallizing Solvent |
|---|---|---|---|
| $CH_3$ | 88–89 | $(CH_3O)_2SO_2$ + NaOH | — |
| $(CH_3)_2CH-$ | 114–118 | A | Hexane |
| $(CH_3)_2CHCH_2-$ | 60–61 | A | Hexane |
| $C_2H_5CH(CH_3)-$ | 93–94 | A | Methanol |
| $CH_3(CH_2)_4-$ | 68 | A | Hexane |
| $CH_3(CH_2)_5-$ | oil | A | Chromatographed on silica gel with benzene, |

TABLE III-continued

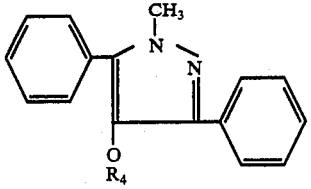

| R4 | Melting Point °C | Method | Recrystallizing Solvent |
|---|---|---|---|
| CH$_3$(CH$_2$)$_6$— | oil | A | followed by recrystallization from hexane Chromatographed, silica gel, toluene |
| CH$_3$(CH$_2$)$_7$— | oil | A | Chromatographed, silica gel, toluene |
| (CH$_3$(CH$_2$)$_9$— | oil | B | Chromatographed, silica gel, toluene |
| CH$_3$(CH$_2$)$_{12}$— | oil | B | Silica gel, toluene |
| CH$_3$(CH$_2$)$_{15}$— | oil | B | Silica gel, toluene |
| CH$_3$(CH$_2$)$_{17}$— | waxy oil | B | Silica gel, toluene |
| ⌬—CH$_2$— | 95–97 | A | Hexane |
| BrCH$_2$CH$_2$— | 71–72 | C | Silica gel, chloroform and toluene |
| HOCH$_2$CH$_2$— | 112–113 | C | Toluene/hexane |
| CH$_2$=CHCH$_2$— | 58–59 | C | Hexane |
| CH≡CCH$_2$— | 74.5–75 | C | Chromatographed, silica gel, benzene, recrystallization from methanol |
| CH$_2$=CClCH$_2$— | 58–59 | C | Silica gel, toluene |
| ClCH=CHCH$_2$— | oil | C | Silica gel, toluene |
| C$_2$H$_5$OOCCH$_2$— | 73–75 | C | 2-Propanol |

TABLE IV

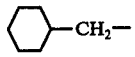

| Z | R4 | Z' | Melting Point °C | Method |
|---|---|---|---|---|
| 2-chloro | n-propyl | H | oil | A |
| 4-chloro | n-propyl | H | 84–86 | A |
| 3-chloro | n-propyl | 3-chloro | oil | A |
| 3-methyl | n-propyl | H | oil | A |
| 4-methyl | n-propyl | H | oil | A |
| 3-methyl | n-propyl | 3-methyl | oil | A |
| 4-methyl | n-propyl | 4-methyl | 78.5–80 | A |
| 4-(n-dodecyl) | n-propyl | H | oil | A |
| 4-(n-butoxy) | n-propyl | H | oil | A |
| 4-phenyl | n-propyl | H | oil gum | A |

TABLE IV-continued

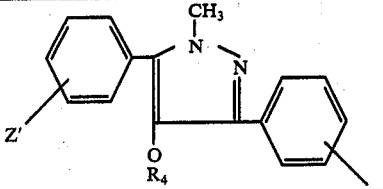

| Z | R4 | Z' | Melting Point °C | Method |
|---|---|---|---|---|

EXAMPLE 9

General Method for Preparation of 4-Benzyloxy-1-methyl-3,5-diphenylpyrazoles.

A mixture of 4-hydroxy-1-methyl-3,5-diphenylpyrazole (0.04 mole), sodium methoxide (0.045 mole) and dry DMF (100 ml) is stirred and heated to 60° C. The reaction mixture is cooled to room temperature and the substituted-benzyl halide (chloride or bromide) (0.05 mole) added dropwise. If the substituted-benzyl halide is a solid, a solution is prepared using dry DMF (50 ml). Stirring is continued and the reaction mixture heated at 55°–60° C until the reaction is complete. The reaction is followed by tlc (CHCl$_3$/silica gel). The mixture is then cooled and poured into an excess of water. The aqueous mixture is made alkaline by the addition of 1N sodium hydroxide and extracted with ether. The ether layer is separated, washed well with water, dried and stripped in vacuo.

The compounds prepared by this method are listed in Table V.

TABLE V

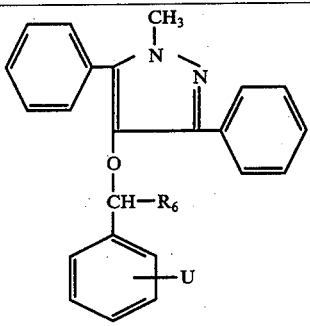

| U | R$_6$ | Melting Point °C | Recrystallizing Solvent |
|---|---|---|---|
| H | H | 128–129.5 | Acetonitrile |
| 2-chloro | H | 64–69 | Eluted on silica gel with CHCl$_3$ |
| 3-chloro | H | 85–86 | Eluted on silica gel with CHCl$_3$, followed by recrystallization from methylcyclohexane |
| 4-chloro | H | oil | Eluted on silica gel with CHCl$_3$ |
| 4-bromo | H | oil | Eluted on silica gel with CHCl$_3$ |
| 2,6-dichloro | H | 110–118 | Methylcyclohexane, |

TABLE V-continued

1-Substituted-4-benzyloxy-3,5-diphenylpyrazole (structure with CH₃ on N, and CH-R₆ with phenyl-U substituent)

| U | R₆ | Melting Point °C | Recrystallizing Solvent |
|---|---|---|---|
| 3,4-dichloro | H | 102–104 | followed by Eluting on silica gel with CHCl₃ Eluted on silica gel with CHCl₃ |
| 4-tert-butyl | H | 107–108 | Eluted on silica gel with benzene, followed by recrystallization from methanol |
| 4-methoxy | H | 71–72 | Eluted on silica gel with benzene, followed by recrystallization from methylcyclohexane |
| 3-trifluoromethyl | H | 84–85 | Hexane |
| 3-cyano | H | 90–92 | Acetonitrile |
| 4-Nitro | H | 84–85 | Eluted on silica gel with CHCl₃, followed by recrystallization from methanol |
| H | Methyl | 132–133 | Methanol |
| H | Phenyl | 106–108 | Eluted on silica gel with benzene |

EXAMPLE 10

Preparation of 3-(p-Chlorophenyl)-4-methoxy-1-methyl-5-phenyl [and 5-(p-Chlorophenyl)-4-methoxy-1-methyl-3-phenyl]-pyrazole.

A mixture of 3-(p-chlorophenyl)-1-methyl-5-phenyl [and 5-(p-chlorophenyl)-1-methyl-3-phenyl]-4-pyrazolol (7.9 g, 0.0278 mole) and 20% aqueous sodium hydroxide solution (200 ml) is stirred and heated to 60° C. Dimethyl sulfate (20.7 ml, 0.222 mole) is added to the turbid yellow solution. An exotherm is observed and the temperature of the reaction mixture rose to 80° C. Stirring is continued and the mixture is allowed to cool to room temperature. A buff-colored gum is formed. The aqueous layer is decanted away from the gum and the gum washed well with water until neutral. The yellow gum, 5.5 g, is dissolved in ether and filtered through a bed of neutral alumina. The filtrate is stripped in vacuo to give a clear yellow oil, which upon standing became a solid. The crude product is slurried with pentane. The product is isolated by filtration and obtained as a white crystalline solid, 2 g (24%), melting point 100°–103° C.

Analyses calculated for $C_{17}H_{15}N_2OCl$: C, 68.33; H, 5.06; N, 9.38; Cl, 11.86. Found: C, 68.18; H, 4.89; N, 9.39; Cl, 12.10.

EXAMPLE 11

General Method for the Preparation of 1-Substituted-4-benzyloxy-3,5-diphenylpyrazoles.

A mixture of 4-benzyloxy-3,5-diphenylpyrazole (0.0278 mole), potassium t-butoxide (0.0306 mole) and 2-propanol (90 ml) is stirred well at room temperature until a clear solution forms. The appropriate alkyl (or arylalkyl) halide (0.0337 mole) is added dropwise. The reaction mixture is stirred for one to two days at room temperature and then is heated at 50° C for 2 to 4 hours. The mixture is poured into water and extracted with chloroform or toluene. The chloroform or toluene layer is separated, washed well with water, dried and stripped in vacuo to give an oil or a solid.

The compounds prepared by this method are listed in Table VI.

TABLE VI

1-Substituted-4-benzyloxy-3,5-diphenylpyrazole (structure with R₁ on N, OCH₂-phenyl at 4-position)

| R₁ | Alkylating Agent | Method of Purification | Melting Point °C |
|---|---|---|---|
| C₂H₅ | C₂H₅I | Eluted on silica gel with chloroform followed by recrystallization from 2-propanol | 54–55 |
| n-C₃H₇ | n-C₃H₇Br | Recrystallized from acetonitrile | 69–70 |
| n-C₅H₁₁ | n-C₅H₁₁Br | — | oil |
| CH₂=CHCH₂— | CH₂=CHCH₂Br | Eluted on silica gel with toluene | oil |
| ⌬—CH₂ | ⌬—CH₂Cl | Recrystallized from 2-propanol | 64.5–68.5 |

EXAMPLE 12

Preparation of 4-(n-Propoxy)-3,5-diphenylpyrazole.

A mixture of 3,5-diphenyl-4-pyrazolol (10 g, 0.042 mole), sodium methoxide (2.27 g, 0.042 mole) and methanol (60 ml) is heated at 60° C for 2 hours. Then 1-bromopropane (5.17 g, 0.042 mole) is added slowly (5 minutes) at 60° C. The reaction mixture is then held at 60° C until the reaction is complete by tlc. The mixture is poured into water and the solid formed is isolated by filtration. Recrystallization of the solid from acetonitrile affords white crystals, 7.4 g (63%), melting point 142°–142.5° C.

Analyses calculated for $C_{18}H_{18}N_2O$: C, 77.67; H, 6.52; N, 10.07. Found: C, 77.46; H, 6.60; N, 9.97.

EXAMPLE 13

Preparation of 4-(Benzyloxy)-3,5-diphenylpyrazole.

A mixture of 3,5-diphenyl-4-pyrazolol (10 g, 0.042 mole), sodium methoxide (2.27 g, 0.042 mole) and methanol (60 ml) is heated at 60° C for 2 hours. Then benzyl chloride is added slowly at 60° C. A white solid forms. Heating is continued overnight at 60° C. The reaction mixture is examined by glc and the reaction is found to be complete. The mixture is poured into water and the solid isolated by filtration. The solid is washed well with water, dried and recrystallized from acetonitrile to give pale yellow crystals, melting point 152°–152.5° C.

Analyses calculated for $C_{22}H_{18}N_2O$: C, 80.95; H, 5.56; N, 8.58. Found: C, 80.77; H, 5.71; N, 8.69.

EXAMPLE 14

Preparation of 1-Methyl-3,5-diphenyl-4-n-propoxypyrazole.

Sodium hydride (57%, 0.92 g, 0.022 mole) is added slowly to a suspension of 1-methyl-3,5-diphenyl-4-pyrazolol (5 g, 0.02 mole) in anhydrous ether (100 ml). An off-white precipitate forms. After stirring for 45 minutes, the solid is removed by filtration, added to dry DMF (30 ml) and treated with 1-iodopropane (5 ml, 0.05 mole). The reaction mixture is stirred, heated at 60° C for 14 hours and then poured into ice water (600 ml). After standing for 24 hours in the refrigerator, a tacky yellow solid is formed. Recrystallization from hexane at −20° C affords an off-white solid, melting point 56°–57° C.

Analyses calculated for $C_{19}H_{20}N_2O$: C, 78.05; H, 6.90; N, 9.58. Found: C, 78.04; H, 6.90; N, 9.49.

EXAMPLE 15

Preparation of 4-n-Butoxy-1-methyl-3,5-diphenylpyrazole.

A mixture of 1-methyl-3,5-diphenyl-4-pyrazolol (25 g, 0.1 mole), sodium hydroxide (56 g, 1.4 mole) and water (800 ml) is stirred until all the sodium hydroxide dissolved. The reaction mixture was heated, filtered and the filtrate stirred vigorously, and 1-iodobutane (22.8 ml, 0.2 mole) added dropwise. The reaction mixture is refluxed for 22 hours. Acetonitrile (700 ml) is added to the reaction mixture to give a homogeneous solution and more 1-iodobutane (10 ml, 0.09 mole) added. After refluxing for 3 hours, the reaction mixture is cooled, extracted with ether and the ether layer separated. The ether layer is washed well with water, dried and stripped in vacuo to give a viscous orange oil, 24.35 g.

The oil is dissolved in hexane (35 ml), filtered through neutral alumina and the filtrate stored overnight at 0° C. Pale yellow crystals formed and are isolated by filtration and dried to give a solid, 7.0 g (23%), melting point 48°–49.5° C.

Analyses calculated for $C_{20}H_{22}N_2O$: C, 78.40; H, 7.24; N, 9.14. Found: C, 78.61; H, 7.53; N, 9.25.

EXAMPLE 16

Preparation of 4-[(Heptyloxy)methoxy]-1-methyl-3,5-diphenylpyrazole.

Anhydrous hydrochloric acid gas is bubbled through a well stirred solution of 1-heptanol (5.8 g, 0.05 mole), para-formaldehyde (1.5 g, 0.05 mole) and methylene chloride (100 ml) at −20° C. An exotherm is observed.

The temperature is maintained at −20° C to −10° C during the addition. When the exotherm subsides, the addition of gas is discontinued and the reaction mixture allowed to warm up to 5°–10° C. The reaction mixture is washed with chilled water (100 ml) and the organic layer separated. The organic layer is filtered through calcium chloride and added to a solution of the sodium salt of 1-methyl-3,5-diphenyl-4-pyrazolol in DMF. The 4-pyrazolol solution is prepared by stirring 1-methyl-3,5-diphenyl-4-pyrazolol (10 g, 0.04 mole) with sodium methoxide (2.16 g, 0.04 mole) and dry DMF (100 ml).

The combined reaction mixture is stirred for 1½ hours and then poured into water (500 ml). The mixture is stirred for 15 minutes and then allowed to settle. The upper aqueous layer is decanted and the lower organic layer diluted with methylene chloride. The methylene chloride solution is washed with 10% aqueous sodium hydroxide (200 ml) and then with water (100 ml). The organic layer is separated and stripped in vacuo. The oil residue is slurried with water (100 ml) and extracted with hexane. The hexane layer is separated and stripped in vacuo to give an oil, 11 g (75%).

Analyses calculated for $C_{24}H_{20}N_2O_2$: C, 76.15; H, 7.99; N, 7.40. Found: C, 75.21; H, 8.02; N, 6.99.

EXAMPLE 17

Preparation of 4-tert-Butoxy-1-methyl-3,5-diphenylpyrazole.

4-Bromo-1-methyl-3,5-diphenylpyrazole (31.3 g, 0.1 mole) and dry tetrahydrofuran (250 ml) are stirred under a nitrogen atmosphere and cooled to −30° C to −40° C. A solution of n-butyllithium (50 ml, 2.4 moles) is added and the deep red solution formed is stirred for ½ hours and allowed to warm to −20° C. The reaction mixture is cooled to −60° C, and a solution of tert-butylperoxybenzoate (19.4 g, 0.1 mole) and dry tetrahydrofuran (50 ml) added dropwise over a ½ hour period. During the addition, the reaction mixture became dark and then lighter in color. The mixture is stirred for ½ hour at −60° C and a solid is formed. The mixture is poured into 10% aqueous hydrochloric acid (400 ml) and the mixture stirred for 10 minutes. The upper organic layer is separated, washed consecutively with 10% aqueous hydrochloric acid (100 ml), with water, with 4% aqueous sodium hydroxide solution (2 × 200 ml) and finally with water. The organic layer is separated and treated with hexane (200 ml). A solid forms, and is removed by filtration.

Stripping of the mother liquor in vacuo affords an oil. The oil is chromatographed on silica gel with toluene. A major component is isolated and recrystallized from hexane to give 4-tert-butoxy-1-methyl-3,5-diphenylpyrazole, 1.0 g (3.4%), melting point 106°–107.5° C.

Analyses calculated for $C_{20}H_{22}N_2O$: C, 78.40; H, 7.34; N, 9.14. Found: C, 78.37; H, 7.22; N, 9.10.

EXAMPLE 18

Preparation of 4-(2-Iodoethoxy)-1-methyl-3,5-diphenylpyrazole.

A mixture of 4-(2-bromoethoxy)-1-methyl-3,5-diphenylpyrazole (3.57 g, 0.01 mole), potassium iodide (16.6 g, 0.1 mole) and acetone (50 ml) is stirred and refluxed for 24 hours.

The reaction mixture is cooled, filtered and evaporated in vacuo to dryness and the residue dissolved in chloroform. After washing with water, the chloroform layer is separated and evaporated in vacuo to dryness. The solid residue is slurried with hexane, removed by filtration and then dried. Recrystallization from a mixture of benzene and hexane yields a solid melting point 68°–69° C.

Analyses calculated for $C_{18}H_{17}N_2OI$: C, 53.48; H, 4.24; N, 6.93; I, 31.39. Found: C, 54.32; H, 4.51; N, 6.81; I, 30.54.

EXAMPLE 19

Preparation of 3,5-Diphenyl-1-methyl-4-[2-(methylthio)ethoxy]-pyrazole.

An aqueous solution of sodium methylmercaptide is prepared by saturating a solution of sodium hydroxide (1.2 g, 0.03 mole) in water (35 ml) with methyl mercaptan. The sodium methylmercaptide solution is added dropwise to a well stirred solution of 4-(2-bromoethoxy)-1-methyl-3,5-diphenylpyrazole (7.14 g, 0.02 mole), benzyltriethylammonium chloride (1 g) and DMF (100 ml). During the addition an exotherm is observed and the temperature rose to 37° C. The reaction mixture is stirred overnight at room temperature and then poured into ice water (450 ml). The mixture is stirred for one hour and then extracted with chloroform. The chloroform layer is separated and stripped in vacuo to give an oil. The oil is slurried with water (100 ml) and extracted with toluene. The toluene layer is separated and stripped in vacuo to give an oil, 5.4 g (83%).

Analyses calculated for $C_{19}H_{20}N_2OS$: C, 70.35; H, 6.22; N, 8.64; S, 9.87. Found: C, 70.38; H, 6.22; N, 8.74; S, 9.86.

EXAMPLE 20

Preparation of 4-[2-(Benzylthio)ethoxy]-3,5-diphenyl-1-methyl-pyrazole.

The product is prepared in a similar manner to the previous compound using benzyl mercaptan instead of methyl mercaptan. The oil obtained from the chloroform layer is purified by eluting on silica gel with toluene. The product is obtained as an oil, 6.3 g (78.8%).

Analyses calculated for $C_{25}H_{24}N_2SO$: C, 74.98; H, 6.04; N, 7.00; S, 7.99. Found: C, 74.87; H, 6.11; N, 6.88; S, 7.96.

EXAMPLE 21

Preparation of 4-[2-(Heptyloxy)ethoxy]-1-methyl-3,5-diphenyl-pyrazole.

Sodium hydride (0.89 g, 57%, 0.02 mole) is added to a solution of 2-[(1-methyl-3,5-diphenyl-4-pyrazolyl)oxy]ethanol (5.9 g, 0.02 mole) and dry DMF (50 ml). The reaction mixture is stirred and heated to 80°-90° C. The stirred mixture is allowed to cool. This mixture is added to a solution of 1-bromoheptane (9 g, 0.05 mole) and dry DMF (75 ml). After heating at 80°-90° C for 4 hours, the stirred reaction mixture is poured into water.

The aqueous mixture is stirred to 15 minutes and then extracted with chloroform. The chloroform layer is separated, washed with water, filtered through sodium chloride, and evaporated to dryness in a hood. The residue is slurried with hexane (400 ml). A solid forms and is removed by filtration. The filtrate is evaporated to dryness. The residue is dissolved in a mixture of chloroform and toluene (1:1) and chromatographed on silica gel. The product is obtained as an oil, 2.5 g (31.9%).

Analyses calculated for $C_{25}H_{32}N_2O_2$: C, 76.49; H, 8.22; N, 7.14. Found: C, 76.35; H, 8.35; N, 6.99.

EXAMPLE 22

Preparation of 4-[2-(benzylsulfonyl)ethoxy]-3,5-diphenyl-1-methyl-pyrazole

A solution of m-chloroperbenzoic acid (6.09 g, 85%, 0.03 mole) and dry chloroform (75 ml) is added dropwise at 10° C-15° C to a well stirred solution of 3,5-diphenyl-4-[2-benzylthio)ethoxy]-1-methylpyrazole (4.1 g, 0.0102 mole) and dry chloroform (100 ml). After complete addition, the reaction mixture is stirred overnight at room temperature.

The mixture is poured into 5% aqueous sodium hydroxide solution (200 ml) and stirred for 1 hour. The chloroform layer is separated, washed with water and stripped to dryness in vacuo. The residue is dissolved in toluene and eluted on silica gel. The purified product is obtained as a solid and is recrystallized from a mixture of benzene and hexane (3:7) to give 1.5 g (34%), m.p. 101° C to 102° C, Ag IR 44,369.

Analysis calculated for $C_{25}H_{24}N_2SO_3$: C, 69.43; H, 5.59; N, 6.48; S, 7.40. Found: C, 70.41; H, 5.95; N, 6.06; S, 7.08.

EXAMPLE 23

Preparation of 1-Methyl-4-(p-nitrophenoxy)-3,5-diphenylpyrazole

A solution of 4-hydroxy-1-methyl-3,5-diphenyl-pyrazole (10 g, 0.04 mole), potassium t-butoxide (4.5, 0.04 mole) and dry DMF (150 ml) is stirred and heated to 60° C. The green fluorescent solution is cooled to room temperature and p-chloronitrobenzene (6.0 g, 0.038 mole) is added. The dark green solution is heated at 60° C for 24 hours and then poured into water, made alkaline with 1N sodium hydroxide and extracted with ether. The ether layer is separated, washed well with water, dried and stripped in vacuo to give a bright-yellow solid 12.9 g (86.5%), m.p. 85° C to 110° C. The solid is chromatographed on silica gel with benzene to give a yellow crystalline solid 11.3 g, m.p. 74° C to 100° C. Recrystallization from methanol (185 ml) affords white crystals 5.5 g (37%) m.p. 120° C to 122° C.

Analysis calculated for $C_{22}H_{17}N_3O_3$: C, 71.15; H, 4.61; N, 11.32. Found: C, 70.55; H, 4.65; N, 11.20.

A second crop 2.35 g (15.8%), m.p. 119° C to 120° C is obtained by chilling the mother liquor.

EXAMPLE 24

Preparation of 4-(p-Aminophenoxy)-1-methyl-3,5-diphenylpyrazole

Hydrazine hydrate (3 ml, 60% solution) is added to a well stirred mixture of 1-methyl-4-(p-nitrophenoxy)-3,5-diphenylpyrazole (2.56 g, 0.0069 mole), 5% Pd on carbon (0.4 g) and absolute ethanol (40 ml). Gas bubbles form immediately and an exotherm (ca. 50° C) is observed. After the reaction subsides, the reaction mixture is refluxed for 2 hours. The reaction mixture is cooled slightly and filtered to remove the catalyst. The filtrate is stripped in vacuo to give a white solid 2.4 g (100%), m.p. 167° C to 169° C. Recrystallization from benzene (20 ml) affords a white solid m.p. 167° C to 168° C.

Analysis calculated for $C_{22}H_{19}N_3O$: C, 77.39; H, 5.61; N, 12.31. Found: C, 78.39; H, 5.85; N, 11.99.

EXAMPLE 25

Preparation of 4-(p-Chlorophenoxy)-1-methyl-3,5-diphenylpyrazole

A solution of sodium nitrite (3.1 g, 0.0422 mole) in water (10 ml) is added slowly at 0° C to 5° C to a well stirred, chilled solution of 4-(p-aminophenoxy)-1-methyl-3,5-diphenylpyrazole (15.1 g, 0.0442 mole) in concentrated hydrochloric acid (50 ml).

This cold reaction mixture is added at 0° C to 5° C to a well stirred, chilled solution of cuprous chloride (4.85 g, 0.049 mole) in concentrated hydrochloride acid (50 ml). The reaction mixture is held at 0° C for half hour, then allowed to warm up to room temperature and finally heated on a steambath for half hour. The reaction mixture is cooled and the solid isolated by filtration.

The tan solid 16.1 g is chromatographed silica gel with chloroform to give a white solid 9.7 g (54.9%), m.p. 99° C to 102° C.

Analysis calculated for $C_{22}H_{17}ClN_2O$: C, 73.22; H, 4.75; N, 7.77; Cl, 9.83. Found C, 72.98; H, 4.61; N, 7.67; Cl, 9.78.

EXAMPLE 26

Preparation of 4-(n-Butylthio)-1-methyl-3,5-diphenylpyrazole

A mixture of 4-bromo-1-methyl-3,5-diphenylpyrazole (21 g, 0.0671 mole), copper(1)salt of butanethiol (12.58 g, 0.08 mole), pyridine (10 ml) and quinoline (100 ml) is stirred and heated at 175° C to 180° C for 8 hours. The reaction mixture is cooled, poured into dilute hydrochloric acid (500 ml) and extracted with benzene. The benzene layer is separated and stripped in vacuo to give a brown oil. The oil is slurried with petroleum ether (b.p. 40° C to 60° C), filtered and the filtrate stripped in vacuo to give a brown syrup 21 g (97%), >95% pure by glc.

Analysis calculated for $C_{20}H_{22}N_2S$: C, 74.51; H, 6.88; N, 8.69. Found: C, 73.91; H, 6.75; N, 8.74.

EXAMPLE 27

Preparation of 1-Methyl-3,5-diphenyl-4-(phenylthio)pyrazole

A mixture of 4-bromo-1-methyl-3,5-diphenylpyrazole (21.84 g, 0.07 mole), copper(1)salt of benzenethiol (14.67 g, 0.085 mole), pyridine (10 ml) and quinoline (100 ml) is stirred and heated at 175° C to 185° C (reflux) for 8 hours. The reaction mixture is allowed to stand overnight at room temperature. The mixture is poured into dilute hydrochloride acid and extracted with benzene. The benzene layer is separated and stripped in vacuo to give a brown syrup. The syrup is extracted with a hot mixture of n-hexane and n-heptane and filtered. The cooled filtrate yields a gray colored solid m.p. 109° C to 110° C. Recrystallization from n-hexane affords white crystals 17.35 g (74.5%), m.p. 109° C to 110° C.

Analysis calculated for $C_{22}H_{18}N_2S$: C, 77.17; H, 5.30; N, 8.18; S, 9.35. Found: C, 77.05, H, 5.16; N, 8.20; S, 9.43.

EXAMPLE 28

Preparation of 4-(n-Butylsulfonyl)-1-methyl-3,5-diphenylpyrazole

A solution of m-chloroperbenzoic acid (10.15 g, 85%, 0.05 mole) in dry chloroform (100 ml) is added to 4-(n-butylthio)-1-methyl-3,5-diphenylpyrazole (6.5g, 0.02 mole) in dry chloroform (50 ml) and the reaction mixture stirred overnight at 10° C to 12° C. The mixture is poured into 10% aqueous sodium hydroxide (200 ml) and extracted with chloroform. The chloroform layer is separated, dried and stripped in vacuo to give a light-orange oil. The oil is chromatographed on silica gel with benzene. The fractions containing the product are combined, stripped in vacuo, extracted with methanol, filtered, stripped in vacuo and then recrystallized from hexane to give a white fluffy solid 4.37 g (61%), m.p. 92.5° C to 93° C.

Analysis calculated for $C_{20}H_{22}N_2SO_2$: C, 67.78; H, 6.26; N, 7.91; S, 9.04. Found: C, 68.01; H, 6.30; N, 7.98; S, 9.14.

EXAMPLE 29

Preparation of 1-Methyl-3,5-diphenyl-4-(phenylsulfonyl)pyrazole

At a temperature of 9° C a solution of m-chloroperbenzoic acid (10.15 g, 85%, 0.05 mole) in dry chloroform (50 ml) is added to a solution of 4-(phenylthio)-1-methyl-3,5-diphenylpyrazole (6.84 g, 0.02 mole) in dry chloroform (50 ml). The reaction mixture is stirred for 3 hours at 9° C and then overnight at room temperature. A heavy precipitate forms. The mixture is treated with 2% aqueous sodium hydroxide and extracted with chloroform. The chloroform layer is separated and stripped in vacuo to give an oil. Trituration of the oil with cyclohexane affords crystals 6.8 g (91%), m.p. 135° C to 141° C. Recrystallization from a mixture of benzene and pentane gave white crystals, m.p. 149° C to 150° C.

Analysis calculated for $C_{22}H_{18}N_2SO_2$: C, 70.58; H, 4.85; N, 7.48; S, 8.55. Found: C, 70.86; H, 5.12; N, 7.23; S, 8.39.

EXAMPLE 30

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about 2 weeks. The test compounds are dispersed in 50/50 acetone/water mixtures containing 0.5% TWEEN® 20, a polyoxyethylene sorbitan monolaurate surfactant by Atlas Chemical Industries, in sufficient quantity to provide the equivalent of about 0.5 lb to 10 lbs per acre of active compound when applied to the plants through a spray nozzle operating at 40 psi for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in Table VII, where it can be seen that the compounds are effective for the control of a variety of broadleaf weeds and grass weeds and with selected compounds effective for controlling barnyardgrass. The specificity of certain compounds is demonstrated by the findings that wheat, barley or rice are not injured or only very mildly affected by selected compounds at rates which provide effective control of the broadleaf weeds and grasses, particularly barnyardgrass.

| Rating System: | % Difference in Growth from the Check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth; that is, a definite physiological malformation but with an over-all effect less than a 5 on the rating scale. | |

*Based on visual determination of stand, size, vigor, chlorosis, growth malformation and over-all plant appearance.

Plant Abbreviations:
SE — Sesbania (*Sesbania exaltata*)
LA — Lambsquarters (*Chenopodium album*)
MU — Mustard (*Brassica kaber*)
PI — Pigweed (*Amaranthus retroflexus*)
BA — Barnyardgrass (*Echinochloa crusgalli*)
CR — Crabgrass (*Digitaria sanguinalis*)
GRF — Green foxtail (*Setaria viridis*)
WO — Wild oats (*Avena fatua*)
VL — Velvetleaf (*Abutilon theophrasti*)
TW — Teaweed (*Sida spinosa*)
RAG — Ragweed (*Ambrosia artemisiifolia*)
WH — Wheat (*Triticum vulgare*)
MG — Morningglory (*Ipomoca purpurea*)
BR — Barley (*Hordeum vulgare*)
RI — Rice (*Oryza sativa*)

TABLE VII

Postemergence Herbicidal Activity

| Compound | Treatment lb/Acre | SE | LA | MU | PI | RAG | MG | BA | CR | GRF | WO | VL | TW | BR | RI | WH |
|---|---|---|---|---|---|---|---|---|---|---|---|---|---|---|---|---|
| 4-Allyloxy-1,2-dimethyl-3,5-diphenylpyrazolium perchlorate | 10 | — | 9 | 9 | 9 | 0 | 5 | 2 | 2 | 0 | 2 | 7 | — | — | — | — |
| | 4 | — | — | 9 | 9 | — | 1 | 3 | 2 | 1 | 0 | — | — | 0 | 5 | 0 |
| | 1 | — | — | 9 | 9 | — | 0 | 2 | 1 | 1 | 0 | — | — | 0 | 3 | 0 |
| 1,2-Dimethyl-3,5-diphenyl-4-n-propoxypyrazolium perchlorate | 9 | — | 9 | 9 | 9 | 9 | 9 | 3 | 5 | 5 | 3 | 9 | — | — | — | — |
| | 4 | — | 9 | 9 | 9 | 8 | 9 | 3 | 3 | 3 | 3 | 6 | — | 0 | 2 | 0 |
| | 1 | — | 9 | 9 | 9 | 3 | 8 | 2 | 2 | 1 | 2 | 6 | — | 0 | 0 | 0 |
| 1,2-Dimethyl-3,5-diphenyl-4-(2-propynyloxy)pyrazolium perchlorate | 4 | — | — | 7 | 9 | — | 6 | 3 | 2 | 1 | 8 | 5 | — | 1 | — | 2 |
| | 1 | — | — | 5 | 8 | — | 1 | 2 | 0 | 1 | 3 | 3 | — | 1 | — | 2 |
| | 0.5 | — | — | 3 | 2 | — | 0 | 1 | 0 | 0 | 0 | 3 | — | 0 | — | 0 |
| 4-Methoxy-1,2-dimethyl-3,5-diphenylpyrazolium perchlorate | 4 | — | — | 9 | 9 | — | 9 | 9 | 9 | 3 | 8 | 8 | — | 0 | 7 | 0 |
| | 1 | — | — | 9 | 8 | — | 0 | 8 | 6 | 0 | 6 | 9 | — | 0 | 0 | 0 |
| | 0.5 | — | — | 9 | 3 | — | 0 | 9 | 5 | 0 | 0 | 5 | — | 0 | 0 | 0 |
| 1,2-Dimethyl-3,5-diphenyl-4-(2-propynyloxy)-pyrazolium methyl sulfate | 4 | 8* | — | 9 | 9 | — | 9 | 5 | 7 | 2 | 6 | 8* | 5* | 1 | 8* | 0 |
| | 1 | 6* | — | 8 | 9 | — | 7 | 5 | 5 | 1 | 5 | 5* | 5* | 0 | 2* | 0 |
| | 0.5 | 2* | — | 8 | 9 | — | 7 | 2 | 1 | 0 | 0 | 2* | 1* | 0 | 1* | 0 |
| 4-Methoxy-1,2-dimethy-3,5-diphenylpyrazolium methyl sulfate | 4 | 8 | — | — | 9 | — | 9 | 8 | 5 | 2 | 8 | 9 | 8 | — | 9 | — |
| | 1 | 3 | — | — | 9 | — | 8 | 8 | 2 | 1 | 7 | 8 | 3 | — | 7 | — |
| | 0.5 | 2 | — | — | 3 | — | 3 | 3 | 2 | 3 | 2 | 9 | 2 | — | 9 | — |
| 4-Ethoxy-1,2-dimethyl-3,5-diphenylpyrazolium perchlorate | 4 | 9 | — | 9 | 9 | 2 | 8 | 8 | 8 | 5 | — | 8 | 8 | — | 3 | — |
| | 1 | 5 | — | 9 | 9 | 2 | 3 | 7 | 6 | 3 | — | 3 | 3 | — | 1 | — |
| | 0.5 | 3 | — | 9 | 9 | 0 | 1 | 7 | 5 | 1 | — | 2 | 7 | — | 0 | — |
| 4-Methoxy-1,2-dimethyl-3,5-diphenylpyrazolium bromide | 4 | 9 | — | 9 | 9 | — | 6 | 8 | 7 | 3 | 2+ | 9 | 9 | — | 9 | — |
| | 1 | 7 | — | 9 | 9 | — | 6 | 9 | 3 | 1 | 1+ | 9 | 9 | — | 8 | — |
| | 0.5 | 3 | — | 8 | 9 | — | 2 | 9 | 1 | 1 | 0+ | 9 | 7 | — | 3 | — |
| 4-Methoxy-1,2-dimethyl-3,5-diphenylpyrazolium iodide | 4 | 9 | — | 9 | 9 | — | 6 | 9 | 8 | 6 | 7+ | 9 | 9 | — | 7 | — |
| | 1 | 3 | — | 9 | 9 | — | 3 | 8 | 8 | 6 | 1+ | 9 | 9 | — | 6 | — |
| | 0.5 | 3 | — | 8 | 8 | — | 2 | 7 | 1 | 1 | 0+ | 8 | 6 | — | 3 | — |
| 4-Benzyloxy-1,2-dimethyl-3,5-diphenylpyrazolium perchlorate | 10 | 7 | — | 8 | 9 | 0 | 1 | 0 | 0 | 0 | 0 | 6 | | | | |
| | 4 | | | 8 | 9 | | 7 | 1 | 6 | 1 | 0 | 6 | | | | |
| | 1 | | | 8 | 9 | | 6 | 1 | 6 | 1 | 0 | 5 | | | | |
| | 0.5 | | | 7 | 9 | | 3 | 0 | 2 | 1 | 0 | 0 | | | | |
| 4-Benzyloxy-1,2-dimethyl-3,5-diphenylpyrazolium methyl sulfate | 10 | 8 | | 9 | 9 | 0 | 6 | 3 | 2 | 3 | 2 | 9 | | | | |
| | 3 | 8 | | 9 | 9 | 5 | 2 | 2 | 2 | 2 | 1 | 6 | | | | |
| | 1 | 0 | | 9 | 8 | 0 | 3 | 1 | 1 | 1 | 0 | | | | | |
| 3,5-Diphenyl-1-Ethyl-4-methoxy-2-methylpyrazolium perchlorate | 10 | 5 | | 9 | 9 | 7 | 9 | 8 | 1 | 2 | 5 | 9 | 9 | | | |
| | 4 | 7 | | | 8 | | 6 | | 1 | 1 | 0 | 2 | 8 | | 1 | |
| 3,5-Diphenyl-4-methoxy-2-methyl-1-n-propylpyrazolium perchlorate | 10 | 7 | | 7 | 9 | 2 | 5 | 5 | 1 | 2 | 5 | 2 | 0 | | | |
| | 4 | 5 | | | 9 | | 1 | | 0 | 0 | 1 | 1 | 6 | | 5 | |
| 1-Benzyl-3,5-diphenyl-4-methoxy-2-methylpyrazolium methyl sulfate | 10 | 8 | | 9 | 9 | 9 | 5 | 3 | 3 | 5 | 6 | 9 | 9 | | | |
| | 4 | 9 | | 9 | 9 | 8 | 9 | 2 | 2 | 2 | 2 | 7 | 8 | | | |
| 1-Benzyl-3,5-diphenyl-4-methoxy-2-methylpyrazolium perchlorate | 10 | 8 | | 9 | 9 | 9 | 2 | 6 | 3 | 6 | 3 | 5 | 9 | | | |
| | 4 | 3 | | 9 | 8 | 8 | 1 | 2 | 1 | 1 | 2 | 2 | 9 | | | |
| | 1 | 1 | | 9 | 7 | 9 | 0 | 0 | 0 | 0 | 0 | 1 | 7 | | | |
| 1,2-Dimethyl-3,5-diphenyl-4-n-propoxypyrazolium methyl sulfate . H₂O | 10 | 6 | | 9 | 9 | 9 | 1 | 5 | 3 | 6 | 7 | 6 | 9 | | | |
| | 4 | 9 | | 9 | 9 | 9 | 5 | 2 | 2 | 2 | 7 | 9 | 8 | | 3 | |
| | 1 | 5 | | 9 | 9 | 0 | 5 | 1 | 1 | 1 | 2 | 6 | 7 | | 1 | |
| 1,2-Dimethyl-3,5-diphenyl-4-n-propoxypyrazolium chloride | 10 | 7 | | 9 | 9 | 9 | 5 | 2 | 1 | 2 | 7 | 9 | 9 | | | |
| | 4 | 9 | | 9 | 9 | 9 | 6 | 1 | 1 | 2 | 6 | 7 | 7 | | 2 | |
| | 1 | 2 | | 9 | 7 | 0 | 3 | 1 | 1 | 1 | 2 | 3 | 6 | | 2 | |
| 1,2-Dimethyl-3,5-diphenyl-4-n-propoxypyrazolium bromide | 10 | 6 | | 9 | 9 | | 3 | 3 | 2 | 1 | 6 | 3 | 9 | | | |
| | 4 | 8 | | 9 | 9 | 9 | 7 | 5 | 2 | 5 | 6 | 7 | 8 | | 2 | |
| 1,2-Dimethyl-3,5-diphenyl-4-i-propoxypyrazolium methyl sulfate . H₂O | 10 | 8 | | 9 | 9 | 6 | 5 | 3 | 5 | 1 | 3 | 8 | 7 | | | |
| | 4 | 9 | | 9 | 9 | 9 | 9 | 7 | 6 | 5 | | 8 | 6 | | 5 | |
| | 1 | 3 | | 9 | 9 | 0 | 3 | 5 | 5 | 2 | | 2 | 2 | | 5 | |
| 1,2-Dimethyl-3,5-diphenyl-4-i-propoxypyrazolium perchlorate | 10 | 8 | | 9 | 9 | 2 | 9 | 6 | 5 | 3 | 5 | 5 | 9 | | | |
| | 4 | 7 | | 9 | 9 | 5 | 3 | 3 | 5 | 7 | | 7 | 1 | | 7 | |
| | 1 | 7 | | 9 | 9 | 3 | 5 | 5 | 2 | 3 | | 5 | 5 | | 5 | |
| 1,2-dimethyl-3,5-diphenyl-4-n-propoxypyrazolium iodide | 10 | 9 | | 9 | 9 | 1 | 2 | 2 | 2 | 2 | 5 | 8 | 8 | | | |
| | 4 | 9 | | 9 | 9 | 9 | 7 | 5 | 6 | 7 | | 8 | 7 | | 6 | |
| | 1 | 5 | | 9 | 9 | 9 | 1 | 2 | 1 | 2 | | 5 | 2 | | 5 | |
| | 0.5 | 1 | | 9 | 9 | 5 | 1 | 1 | 1 | 5 | | 3 | 0 | | 3 | |
| 4-n-Butoxy-1,2-dimethyl-3,5- | 10 | 8 | | 9 | 9 | 9 | 5 | 3 | 3 | 7 | 7 | 6 | 9 | | | |

TABLE VII-continued

Postemergence Herbicidal Activity

| Compound | Treatment lb/Acre | SE | LA | MU | PI | RAG | MG | BA | CR | GRF | WO | VL | TW | BR | RI | WH |
|---|---|---|---|---|---|---|---|---|---|---|---|---|---|---|---|---|
| diphenylpyrazolium perchlorate | 4 | 9 | | 9 | 9 | 9 | 5 | 5 | 6 | 6 | | 3 | 7 | | 6 | |
| | 1 | 7 | | 9 | 9 | 8 | 3 | 5 | 6 | 3 | | 2 | 3 | | 6 | |
| | 0.5 | 7 | | 8 | 9 | 8 | 3 | 2 | 2 | 1 | 1 | 3 | 5 | | 3 | |
| 4-n-Butoxy-1,2-dimethyl-3,5-diphenylpyrazolium methyl sulfate . H$_2$O | 10 | 7 | | 9 | 9 | 9 | 9 | 3 | 3 | 3 | | 8 | 8 | | 5 | |
| | 4 | 9 | | 9 | 9 | 9 | 2 | 5 | 3 | 1 | | 8 | 3 | | 5 | |
| | 1 | 2 | | 9 | 9 | 9 | 3 | 6 | 8 | 8 | 3 | 8 | 7 | | | |
| 1,2-Dimethyl-3,5-diphenyl-4-n-pentyloxypyrazolium perchlorate | 10 | 9 | | 9 | 9 | 9 | 5 | 5 | 3 | 5 | | 6 | 5 | | 3 | |
| | 4 | 9 | | 9 | 8 | 9 | 3 | 2 | 1 | 2 | | 3 | 2 | | 3 | |
| | 1 | 9 | | 8 | 5 | 5 | 3 | 3 | 7 | 3 | 3 | 9 | 6 | | | |
| 1,2-Dimethyl-3,5-diphenyl-4-n-pentyloxypyrazolium methyl sulfate . ½ H$_2$O | 10 | 9 | | 9 | 9 | | 7 | 5 | 2 | 5 | | 7 | 6 | | 5 | |
| | 4 | 9 | | 9 | 9 | 9 | 3 | 6 | 1 | 2 | | 3 | 3 | | 5 | |
| | 1 | 6 | | 9 | 8 | 5 | 9 | 5 | 2 | 3 | 2 | 9 | 9 | | | |
| 4-sec-Butoxy-1,2-dimethyl-3,5-diphenylpyrazolium methyl sulfate | 10 | 9 | | 9 | 9 | 9 | 9 | 6 | 1 | 1 | | 9 | 6 | | 6 | |
| | 4 | 9 | | 9 | 8 | 9 | 3 | 3 | 1 | 1 | | 5 | 3 | | 3 | |
| | 1 | 7 | | 9 | 7 | 0 | 7 | 6 | 9 | 6 | 3 | 9 | 9 | | | |
| 4-sec-Butoxy-1,2-dimethyl-3,5-diphenylpyrazolium perchlorate | 10 | 9 | | 9 | 9 | 9 | 7 | 6 | 3 | 1 | | 1 | 1 | | 3 | |
| | 4 | 9 | | 9 | 8 | 9 | 6 | 3 | 1 | 1 | | 1 | 1 | | | |
| 5-(p-Chlorophenyl)-1,2-dimethyl-3-phenyl-4-n-propoxy-pyrazolium methyl sulfate | 10 | 7 | | 9 | 9 | 6 | 5 | 7 | 7 | 5 | 2 | | | | | |
| 4-iso-Butoxy-1,2-dimethyl-3,5-diphenylpyrazolium methyl sulfate | 10 | 8 | | 8 | 9 | 0 | 7 | 8 | 7 | 6 | 3 | 7 | 8 | | | |
| 1,2-Dimethyl-3,5-diphenyl-4-n-hexyloxypyrazolium methyl sulfate | 10 | 9 | | 9 | 9 | 5 | 5 | 6 | 7 | 8 | 2 | 9 | 8 | | | |
| 1,2-Dimethyl-3,5-diphenyl-4-n-heptyloxypyrazolium methyl sulfate | 10 | 9 | | 9 | 5 | 6 | 6 | 6 | 6 | 2 | 6 | 8 | | | | |
| 1,2-Dimethyl-3,5-diphenyl-4-n-octyloxypyrazolium methyl sulfate | 10 | 9 | | 8 | 9 | 5 | 7 | 6 | 6 | 6 | 2 | 6 | 9 | | | |
| | 4 | 8 | | 9 | 9 | 9 | 5 | 7 | 3 | 6 | | 6 | 6 | 2 | | |
| 4-n-Decyloxy-1,2-dimethyl-3,5-diphenylpyrazolium methyl sulfate . H$_2$O | 10 | 8 | | 9 | 9 | 2 | 3 | 6 | 6 | 6 | 1 | 6 | 8 | | 5 | |
| | 4 | 3 | | 7 | 7 | 2 | 3 | 6 | 3 | 3 | | 3 | 2 | | | |
| 1,2-Dimethyl-3,5-diphenyl-4-n-tridecyloxypyrazolium methyl sulfate | 10 | 6 | | 9 | 9 | 3 | 5 | 5 | 6 | 5 | 1 | 5 | 5 | | | |
| | 4 | 3 | | 9 | 7 | 9 | 6 | 3 | 2 | 5 | | 6 | 9 | | | |
| 1,2-Dimethyl-3,5-diphenyl-4-n-hexadecyloxypyrazolium methyl sulfate | 10 | 3 | | 6 | 9 | 1 | 7 | 5 | 5 | 5 | 0 | 4 | 0 | | | |
| 4-Cyclohexylmethoxy-1,2-dimethyl-3,5-diphenylpyrazolium methyl sulfate | 10 | 9 | | 9 | 9 | 7 | 3 | 6 | 8 | 7 | 2 | 6 | 8 | | | |
| | 4 | 5 | | 6 | 7 | 2 | 1 | 1 | 1 | 2 | 1 | 3 | 6 | | | |
| 5-(p-Chlorophenyl)-1,2-dimethyl-4-methoxy-3-phenylpyrazolium methyl sulfate | 10 | 7 | | 8 | 9 | 5 | 5 | 7 | 1 | 2 | 6 | 6 | 6 | | | |
| 1,2-Dimethyl-3,5-diphenyl-4-4-methoxybenzyl oxy-pyrazolium methyl sulfate | 10 | 7 | | 9 | 9 | 0 | 3 | 1 | 1 | 2 | 1 | 5 | 6 | | | |
| 1,2-Dimethyl-4-n-propoxy-3,5-di-p-tolylpyrazolium tetrafluoroborate | 10 | 9 | | 9 | 9 | 5 | 2 | 3 | 7 | 6 | 1 | 5 | 3 | | | |
| 4-(4-Bromobenzyl)oxy-1,2-dimethyl-3,5-diphenylpyrazolium methyl sulfate | 10 | 6 | | 5 | 3 | 2 | 1 | 0 | 1 | 1 | 1 | 2 | 5 | | | |
| 4-(4-Chlorobenzyl)oxy-1,2-dimethyl-3,5-diphenylpyrazolium methyl sulfate | 10 | 7 | | 6 | 5 | 2 | 0 | 3 | 6 | 5 | 2 | 0 | 0 | | | |
| 4-(3-Chlorobenzyl)oxy-1,2-dimethyl-3,5-diphenylpyrazolium methyl sulfate | 10 | 5 | | 8 | 5 | 1 | 1 | 2 | 2 | 3 | 2 | 5 | 5 | | | |
| 1,2-Dimethyl-3,5-diphenyl-4-(3-α,α,α-trifluoromethylbenzyl)oxypyrazolium methyl sulfate | 10 | 3 | | 9 | 8 | 2 | 1 | 1 | 1 | 1 | 1 | 6 | 3 | | | |
| 4-(3-Cyanobenzyl)oxy-1,2-dimethyl-3,5-diphenylpyrazolium methyl sulfate . H$_2$O | 10 | 2 | | 6 | 7 | 0 | 0 | 0 | 0 | 0 | 1 | 3 | 1 | | | |
| 1,2-Dimethyl-3,5-diphenyl-4-(4-methylbenzyl)oxypyrazolium methyl sulfate | 10 | 7 | | 9 | 8 | 2 | 0 | 2 | 2 | 2 | 2 | 6 | 1 | | | |
| 4-(2-Chlorobenzyl)oxy-1,2-dimethyl-3,5-diphenylpyrazolium methyl sulfate | 10 | 6 | | 7 | 7 | 0 | 3 | 1 | 1 | 1 | 1 | 0 | 0 | | | |

\* = Data obtained in separate tests
+ = 6 Week data

We claim:

1. A method for the control of undesirable broad leaf weeds and grass weeds comprising: contacting said weeds with a herbicidally effective amount of a compound selected from the group consisting of: 1,2-dimethyl-3,5-diphenyl-4-methoxypyrazolium perchlorate, 1,2-dimethyl-3,5-diphenyl-4methoxypyrazolium-methyl sulfate, 1,2-dimethyl-3,5-diphenyl-4-n-propoxypyrazolium chloride, 1,2-dimethyl-3,5-diphenyl-4-i- propoxypyrazolium methyl sulfate, 4-n-butoxy-1,2-dimethyl-3,5-diphenylpyrazolium perchlorate and 1,2-dimethyl-3,5-diphenyl-4-n-pentyloxypyrazolium perchlorate.

2. The method according to claim 1, wherein the compound is applied to the foliage of undesirable plants at the rate of from 0.5 pound to 10 pounds per acre of pyrazolium cation.

3. The method for the control of undesirable broadleaf weeds and grass weeds comprising applying to the foliage thereof a herbicidally effective amount of a compound according to claim 1.

4. The method according to claim 1, wherein the compound is 1,2-dimethyl-3,5-diphenyl-4-methoxypyrazolium perchlorate.

5. The method according to claim 1 wherein the compound is 1,2-dimethyl-3,5-diphenyl-4-methoxypyrazolium methyl sulfate.

6. The method according to claim 1 wherein the compound is 1,2-dimethyl-3,5-diphenyl-4-n-propoxypyrazolium chloride.

7. The method according to claim 1 wherein the compound is 1,2-dimethyl-3,5-diphenyl-4-i-propoxypryazolium methyl sulfate.

8. The method according to claim 1 wherein the compound is 4-n-butoxy-1,2-dimethyl-3,5-diphenylpyrazolium perchlorate.

9. The method according to claim 1 wherein the compound is 1,2-dimethyl-3,5-diphenyl-4-m-pentyloxypyrazolium perchlorate.

* * * * *